United States Patent [19]

Bednar et al.

[11] Patent Number: 5,646,000

[45] Date of Patent: Jul. 8, 1997

[54] COMPOUNDS AND METHODS FOR IDENTIFYING ACTIVATED PLATELETS

[75] Inventors: Bohumil Bednar, North Wales; Melissa Egbertson, Ambler; Robert J. Gould, Green Lane; George D. Hartman, Landsdale; Jules A. Shafer, Gwynedd Valley, all of Pa.

[73] Assignee: Merck & Co., Inc., Rahway, N.J.

[21] Appl. No.: 315,034

[22] Filed: Sep. 29, 1994

[51] Int. Cl.$^6$ ............... G01N 33/567; C07D 401/14; C07D 401/06
[52] U.S. Cl. ............... 435/7.21; 436/503; 436/800; 436/811; 546/37; 546/196; 546/200
[58] Field of Search ............... 546/200, 196, 546/37; 435/7.21; 436/503, 800, 811

[56] References Cited

U.S. PATENT DOCUMENTS

| | | | |
|---|---|---|---|
| 5,264,420 | 11/1993 | Duggan et al. | 514/19 |
| 5,272,158 | 12/1993 | Hartman et al. | 514/323 |
| 5,334,596 | 8/1994 | Hartman et al. | 514/301 |
| 5,389,631 | 2/1995 | Claremon et al. | 514/221 |

FOREIGN PATENT DOCUMENTS

| | | |
|---|---|---|
| 0 422 937A1 | 4/1991 | European Pat. Off. . |
| 0 540 334A1 | 5/1993 | European Pat. Off. . |

OTHER PUBLICATIONS

D'Souza, "Platelet activation and arterial thrombosis", The Lancet, Oct. 1994, vol. 344, pp. 991–995.

Glusko et al. "Fibrinogen Receptors in Platelet Adhesion to Surfaces of Extracorporeal Circuit", J. Physiol. 1987, 252:H, pp. 615–621.

*Primary Examiner*—Mary E. Ceperley
*Attorney, Agent, or Firm*—Richard S. Parr; Mary A. Appollina; Melvin Winokur

[57] ABSTRACT

The invention is directed to a series of novel compounds, and their pharmaceutically acceptable salts, of the formula

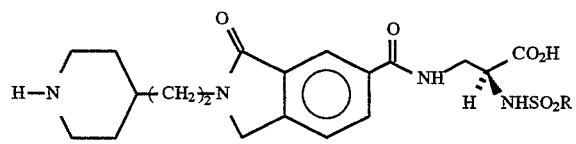

wherein R is $C_{0-6}$ alkyl substituted with $R^5$ or a mono or polycyclic aromatic or heteroaromatic system comprised of 5 or 6-membered aromatic or heteroaromatic rings that are either unsubstituted or substituted with one or more of $R^1$ and $R^2$; $R^1$ and $R^2$ are independently $C_{1-6}$ alkyl, carboxyl, hydroxyl, azido, nitro, amino, $C_{1-6}$ alkylamino, $C_{1-6}$ dialkylamino, arylamino, aryl $C_{1-6}$ alkylamino, hydroxysulfonyl or arylazo; aryl is a phenyl or naphthyl ring which is unsubstituted or substituted with one or more of $R^3$ and $R^4$; $R^3$ and $R^4$ are independently $C_{1-6}$ alkyl, azido, nitro, amino, $C_{1-6}$ dialkylamino or hydroxysulfonyl; $R^5$ is

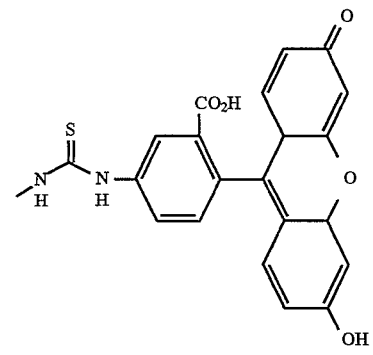

or

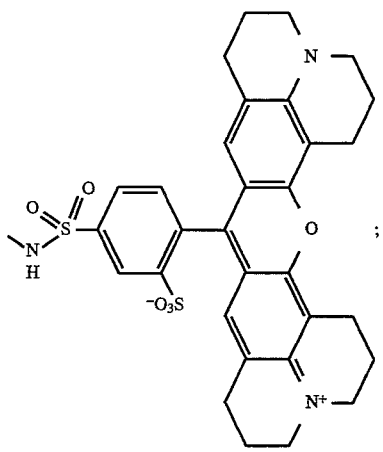

provided that when R is an unsubstituted monocyclic ring, the monocyclic ring is not phenyl or pyridyl. Such compounds are useful as fluorescent probes for identifying antiplatelet agents which selectively bind to activated platelets.

24 Claims, No Drawings

COMPOUNDS AND METHODS FOR IDENTIFYING ACTIVATED PLATELETS

FIELD OF THE INVENTION

The present invention provides novel compounds which are fluorescent probes of glycoprotein IIb/IIIa receptor on platelets useful for distinguishing the "activated" or "unactivated" state of the platelet. More specifically, the compounds of the instant invention can be used to identify antiplatelet agents for treating thrombotic conditions which bind preferentially to activated platelets, thereby minimizing thrombocytopenic potential.

BACKGROUND OF THE INVENTION

Platelets are cell-like anucleated fragments, found in the blood of all mammals, which participate in blood coagulation. Fibrinogen is a glycoprotein present as a normal component of blood plasma. Fibrinogen participates in platelet aggregation and fibrin formation in the blood clotting mechanism. Platelets are deposited at sites of vascular injury where multiple physiological agonists act to initiate platelet aggregation culminating in the formation of a platelet plug to minimize blood loss.

When a blood vessel is damaged either acutely by damage such as wounding or clinical interventions like angioplasty, or more chronically by the pathophysiological processes of arteriosclerosis, platelets are activated to adhere to the disrupted surface and to each other. This activation, adherence and aggregation may lead to occlusive thrombus formation in the lumen of the blood vessel, preventing blood flow and resulting in acute thrombotic syndromes.

Platelet membrane receptors are essential in the process of platelet adhesion and aggregation. Interaction of fibrinogen with a receptor (fibrinogen receptor) on the platelet membrane, a protein complex known as glycoprotein IIb/IIIa (i.e., GP IIb/IIIa, also known as integrin $\alpha_{IIb}\beta_3$) is known to be essential for normal platelet function. More specifically, the final obligatory step in platelet aggregation is the binding of fibrinogen to an activated membrane-bound glycoprotein complex IIb/IIIa. During this platelet activation process, GP IIb/IIIa undergoes an ill-defined change in the spatial orientation of extracellular domains resulting in the exposure of the occult binding sites for fibrinogen. The biochemical processes that underlay conversion of GP IIb/IIIa to the form competent to bind fibrinogen are unknown, however, these conformational changes are paralleled by the exposure of neoepitopes on the GP IIb/IIIa molecule that may be detected with antibodies. The ability of GP IIb/IIIa to undergo this conformational change is an intrinsic property of the protein complex because the activation dependent epitopes may be induced in solubilized and purified GP IIb/IIIa by antibodies and by small molecules.

Thrombocytopenia is a platelet disorder characterized by a decrease in the number of blood platelets (e.g., thrombocytopenia is typically defined as present when the platelet count is below 100,000/µl). Thrombocytopenia may stem from failure of platelet production, sequestration of platelets in the spleen or liver, increased platelet destruction or utilization, or dilution of circulating platelets. Regardless of the cause, severe thrombocytopenia often results in a typical pattern of bleeding. When platelet counts are in the range of 40,000 to 60,000/µl, there may be post traumatic bleeding; and at counts of 20,000/µl, spontaneous hemorrhage is a strong possibility.

More than 80 drugs have been implicated or established as inducers of thrombocytopenia. When the thrombocytopenia is drug-induced, it can have a nonimmune or an immune pathogenesis. Immunologic reactions that terminate in platelet destruction occur when the drug (or one of its derivatives or metabolites) acts as a hapten and forms a complex with the plasma protein. This complex has antigenic properties and induces production of high affinity antibodies. The drug-antibody complex is capable of and sometimes binds to the platelet surface resulting in subsequent removal of the antibody-coated platelets from circulation giving rise to thrombocytopenia.

An alternate mechanism involves direct binding of the drug to the platelet surface, which then exposes antigenic sites to which the antibody binds. The antibody might also bind directly to platelet-bound drug or bind to a drug-platelet membrane complex.

The identification of agents which act as inhibitors of platelet aggregation and which bind selectively to the activated form of platelets and the activated, isolated GP IIb/IIIa is desirable since this type of selective antiplatelet agent would minimize the potential for drug-induced thrombocytopenia.

SUMMARY OF THE INVENTION

The fluorescent probe compounds of the present invention are of the formula wherein R is selected from $C_{0-6}$ alkyl substituted with $R^5$, or a mono- or polycylic aromatic or heteroaromatic system comprised of 5 or 6-membered aromatic or heteroaromatic rings that are either unsubstituted or substituted with one or more of $R^1$ and $R^2$, wherein the heteroaromatic ring contains one to four heteroatoms selected from N, O or S;

$R^1$ and $R^2$ are each independently selected from $C_{1-6}$ alkyl, carboxyl, hydroxyl, azido, nitro, amino, $C_{1-6}$ alkylamino, $C_{1-6}$ dialkylamino, arylamino, aryl $C_{1-6}$ alkylamino, hydroxysulfonyl or arylazo;

aryl is a phenyl or naphthyl ring which is unsubstituted or substituted with one or more of $R^3$ and $R^4$;

$R^3$ and $R^4$ are each independently selected from $C_{1-6}$ alkyl, azido, nitro, amino, $C_{1-6}$ dialkylamino or hydroxysulfonyl; and $R^5$ is

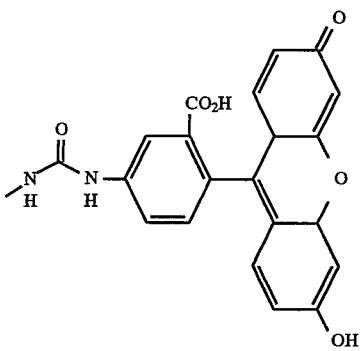

or

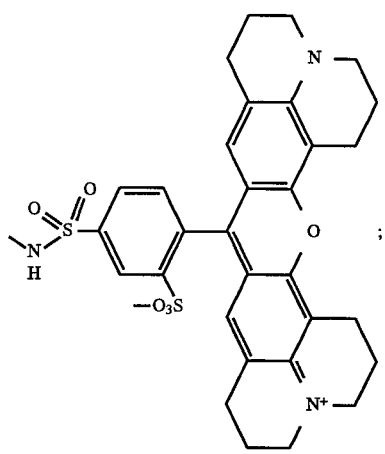

provided that when R is an unsubstituted monocyclic ring, the monocyclic ring is not phenyl or pyridyl; and the pharmaceutically acceptable salts thereof.

In one embodiment of the invention are the compounds wherein R is selected from $C_{0-6}$ alkyl substituted with $R^5$, or a mono- or polycylic aromatic ring system that is either unsubstituted or substituted with one or more of $R^1$ and $R^2$.

In one class are the compounds wherein R is selected from

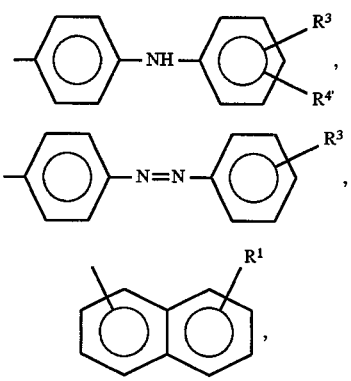

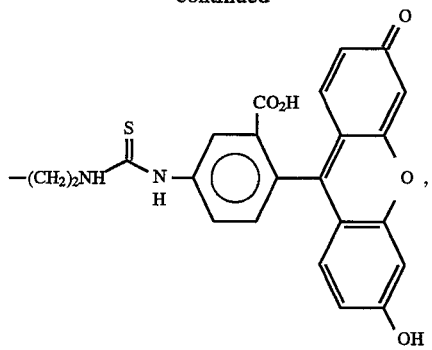

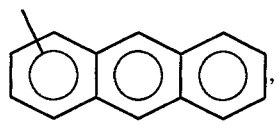

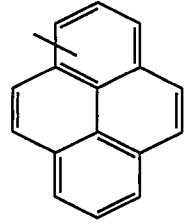

or

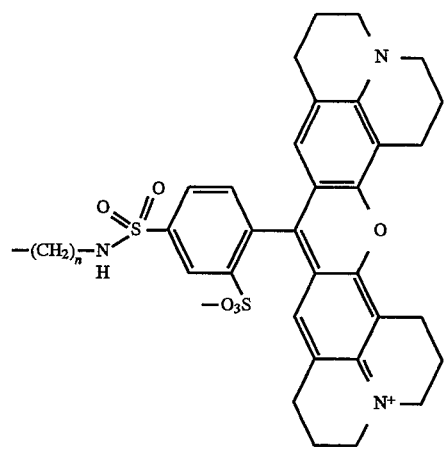

where n is an integer of from 0 to 6.

In a subclass are the compounds wherein $R^1$ is selected from $C_{1-6}$ dialkylamino, arylamino or aryl $C_{1-6}$ alkylamino; and $R^3$ and $R^4$ are each independently selected from $C_{1-6}$ alkyl, nitro, amino or $C_{1-6}$ dialkylamino.

Illustrative of the subclass are the compounds wherein R is selected from

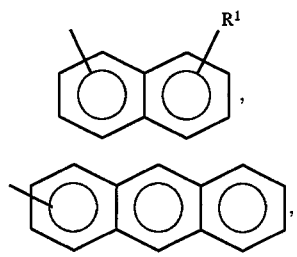

5
-continued

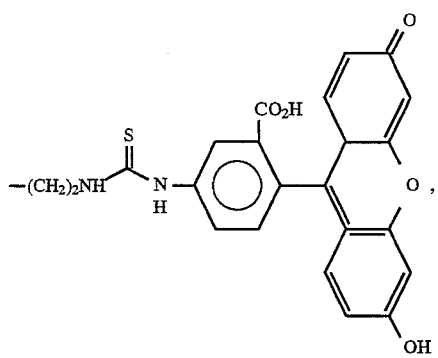

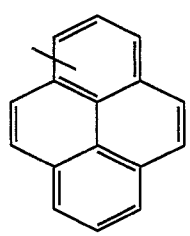

or

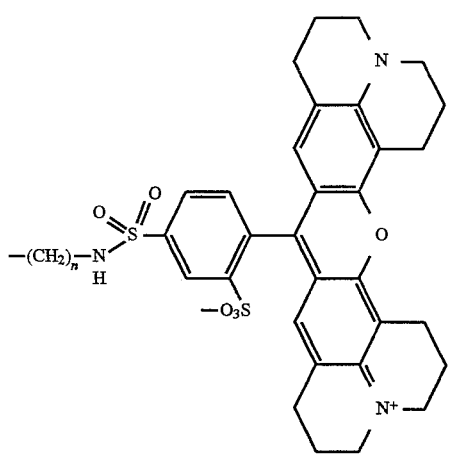

and $R^1$ is $C_{1-6}$ dialkylamino.

Exemplifying the invention are the compounds wherein R is selected from

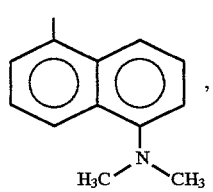

6
-continued

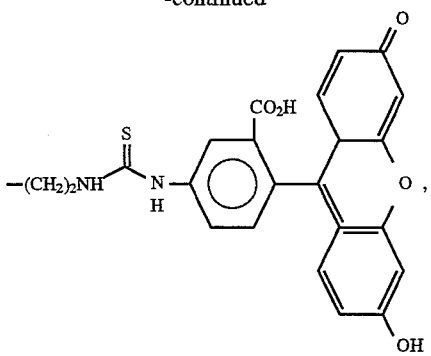

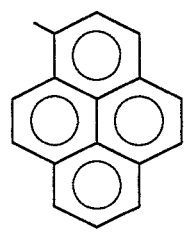

or

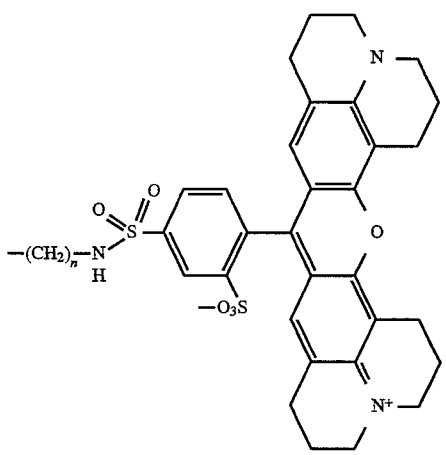

where n is an integer of from 0 to 6.

An example of the invention is a method of identifying an antiplatelet agent that binds preferentially to activated platelets comprising mixing a fluorescent probe compound with a test substance selected from an active form of GP IIb/IIIa, an inactive form of GP IIb/IIIa, an active form of platelets or a resting form of platelets, measuring binding of the fluorescent probe compound to the test substance and displacing the bound fluorescent probe compound with the antiplatelet agent.

More particularly illustrating the invention is the method further comprising the step of calculating the affinity of the antiplatelet agent for the test substance.

Further illustrating the invention is a method of monitoring plasma drug levels of a patient being treated with a GP IIb/IIIa inhibitor compound comprising taking a blood sample from the patient, adding a fluorescent probe compound, measuring the amount of fluorescence and determining the amount of the GP IIb/IIIa inhibitor compound in the blood.

Still another illustration of the invention is a method of monitoring receptor occupancy of the platelets of a patient receiving a GP IIb/IIIa inhibitor compound comprising taking a blood sample from the patient, adding a fluorescent probe compound, measuring the amount of fluorescence and determining the amount of free receptor on the platelets.

More particularly exemplifying the invention is any of the above-described methods (i.e, the method of identifying an antiplatelet agent that binds preferentially to activated platelets, the method of monitoring plasma drug levels of a patient being treated with a GP IIb/IIIa inhibitor compound or the method of monitoring receptor occupancy of the platelets of a patient receiving a GP IIb/IIIa inhibitor compound) wherein the fluorescent probe compound is a compound of the formula

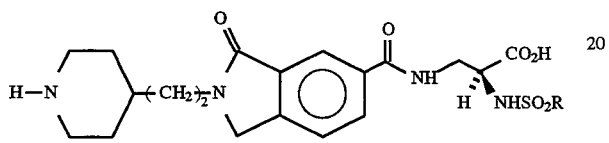

wherein

R is selected from $C_{0-6}$ alkyl substituted with $R^5$, or a mono- or polycylic aromatic or heteroaromatic system comprised of 5 or 6-membered aromatic or heteroaromatic rings that are either unsubstituted or substituted with one or more of $R^1$ and $R^2$, wherein the heteroaromatic ring contains one to four heteroatoms selected from N, O or S;

$R^1$ and $R^2$ are each independently selected from $C_{1-6}$ alkyl, carboxyl, hydroxyl, azido, nitro, amino, $C_{1-6}$ alkylamino, $C_{1-6}$ dialkylamino, arylamino, aryl $C_{1-6}$ alkylamino, hydroxysulfonyl or arylazo;

aryl is a phenyl or naphthyl ring which is unsubstituted or substituted with one or more of $R^3$ and $R_4$;

$R^3$ and $R^4$ are each independently selected from $C_{1-6}$ alkyl, azido, nitro, amino, $C_{1-6}$ dialkylamino or hydroxysulfonyl; and $R^5$ is

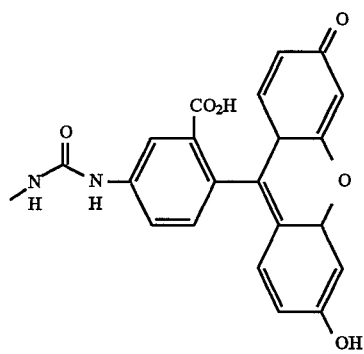

or

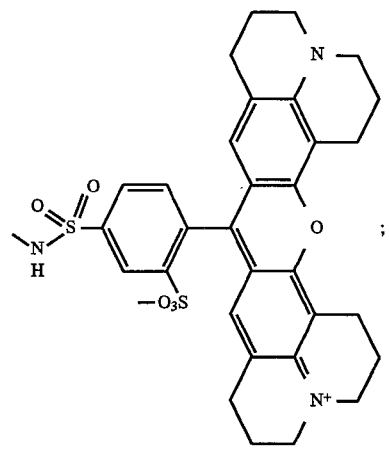

provided that when R is an unsubstituted monocyclic ring, the monocyclic ring is not phenyl or pyridyl; and the pharmaceutically acceptable salts thereof.

An illustration of the invention is any of the above-described methods wherein R is selected from $C_{0-6}$ alkyl substituted with $R^5$, or a mono- or polycylic aromatic ring system that is either unsubstituted or substituted with one or more of $R^1$ and $R^2$.

Another example of the invention is any of the above-described methods wherein R is selected from

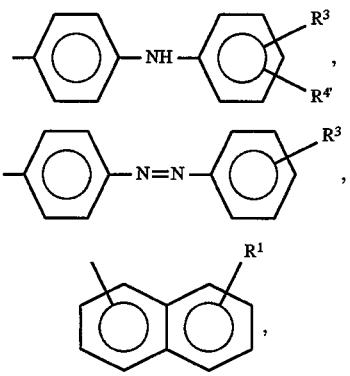

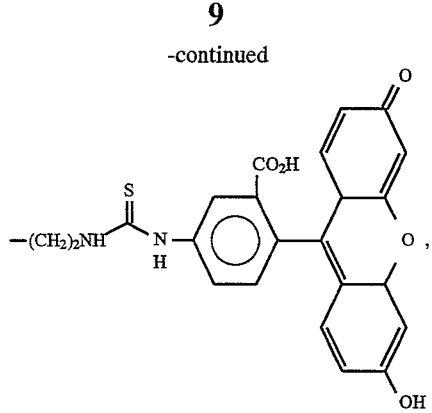

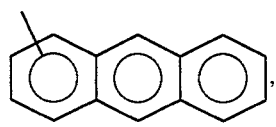

or

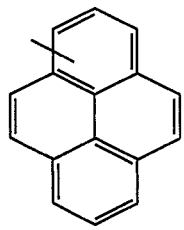

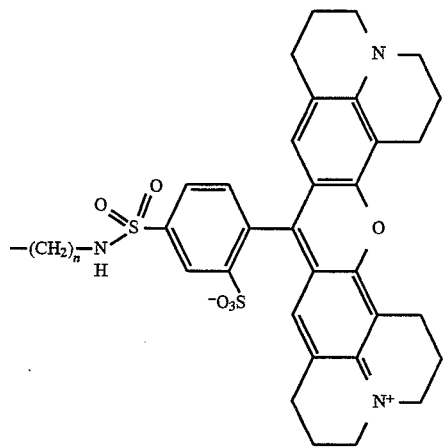

where n is an integer of from 0 to 6.

More specifically exemplifying the invention is any of the above-described methods wherein $R^1$ is selected from $C_{1-6}$ dialkylamino, arylamino or aryl $C_{1-6}$ alkylamino; and $R^3$ and $R^4$ are each independently selected from $C_{1-6}$ alkyl, nitro, amino or $C_{1-6}$ dialkylamino.

More specifically illustrating the invention is any of the above-described methods wherein R is selected from

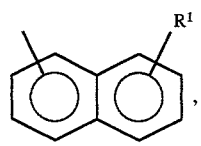

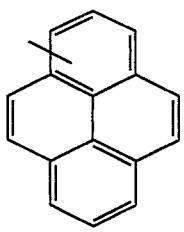

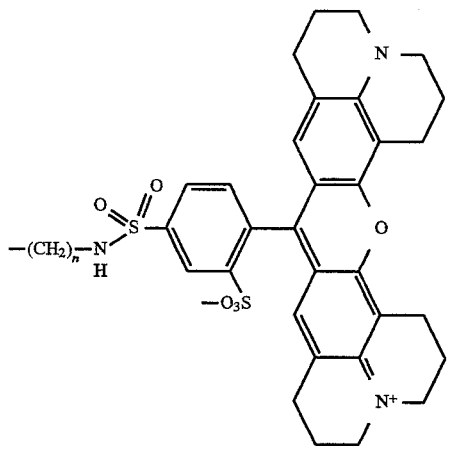

where n is an integer of from 0 to 6 and $R^1$ is $C_{1-6}$ dialkylamino.

Another illustration of the invention is any of the above-described methods wherein R is selected from

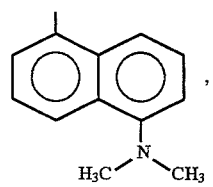

-continued

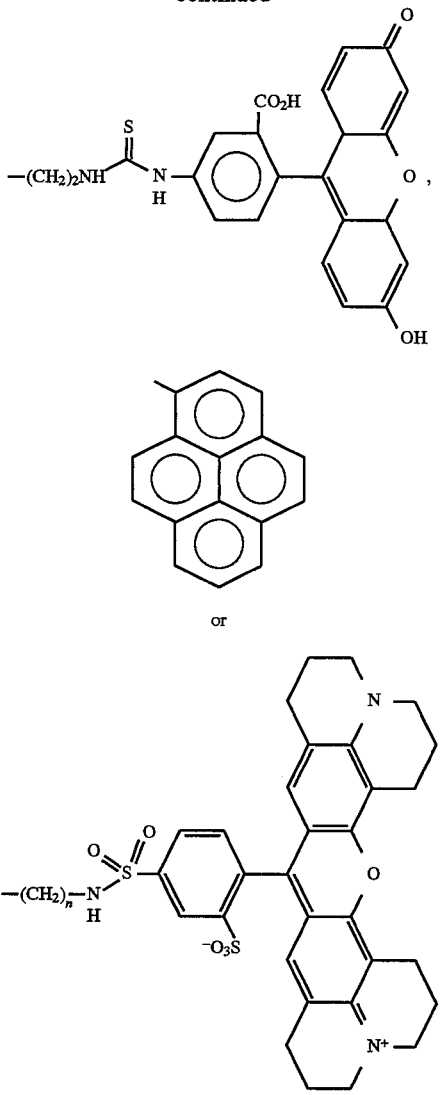

where n is an integer of from 0 to 6.

DETAILED DESCRIPTION OF THE INVENTION

The compounds of the present invention are useful as fluorescent probes to determine the affinity of GP IIb/IIIa inhibitors for the "activated" or "unactivated" forms of platelets and the isolated receptor. GP IIb/IIIa inhibitors are useful in inhibiting the binding of fibrinogen to blood platelets, inhibiting the aggregation of blood platelets, treating thrombus formation or embolus formation, and in the prevention of thrombus formation or embolus formation. GP IIb/IIIa inhibitors are therefore useful as pharmaceutical agents for mammals, especially for humans. More specifically, GP IIb/IIIa inhibitors can be used to prevent or modulate the progress of myocardial infarction, unstable angina and thrombotic stroke, in either acute or chronic settings. In addition they are useful in surgery on peripheral arteries (arterial grafts, carotid endarterectomy) and in cardiovascular surgery where manipulation of arteries and organs and/or the interaction of platelets with artificial surfaces, leads to platelet aggregation and consumption. The aggregated platelets may form thrombi and thromboemboli. GP IIb/IIIa inhibitors can thus be administered to surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GP IIb/IIIa on the platelet membranes and fibrinogen adsorbed to the surface of the circuit (Glusko et al., Amer. J. Physiol., 1987, 252:H, pp. 615–621). Platelets released from artificial surfaces show impaired hemostatic function. GP IIb/IIIa inhibitors can be administered to prevent adhesion.

Other applications of GP IIb/IIIa inhibitors include is prevention of platelet thrombosis, thromboembolism, reocclusion and restenosis during and after thrombolytic therapy and prevention of platelet thrombosis, thromboembolism, reocclusion and restenosis after angioplasty of coronary and other arteries and after coronary artery bypass procedures.

Examples of GP IIb/IIIa inhibitors useful for the above-described utilities are the fibrinogen receptor antagonists disclosed and described in U.S. Pat. No. 5,272,158, issued Dec. 21, 1993; U.S. Pat. No. 5,264,420, issued Nov. 23, 1993; EP 0 422 937, published Apr. 17, 1991; EP 0 540 334 A 1, published May 5, 1993.

The compound referred to as 1-12 in U.S. Pat. No. 5,272,158, i.e., 2,3-Dihydro-N-(2-carboxyethyl)-2-[2-(4-piperidinyl)ethyl]-3-oxo-1-H-isoindole-5-carboxamide, is a potent inhibitor of platelet aggregation. Compound 1-12 in U.S. Pat. No. 5,272,158 will hereafter be referred to as Compound A.

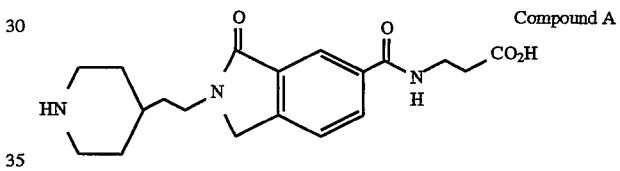

Compound A

The compound referred to as Compound 39a in U.S. Pat. No. 5,264,420 is Pib-Gly-3(R)-[2(indol-3-yl)ethyl]β-alanine hydrogen chloride and is a potent inhibitor of platelet aggregation. Compound 39a in U.S. Pat. No. 5,264,420 will hereafter be referred to as Compound B.

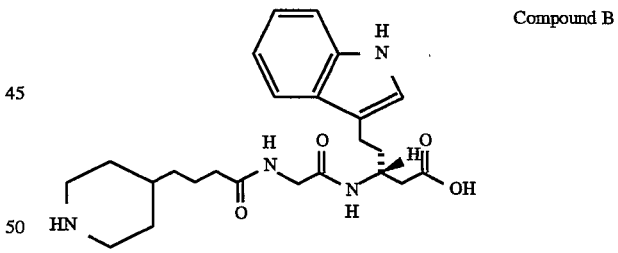

Compound B

The cyclic heptapeptide fibrinogen receptor antagonist

Compound C

Ac—Cys—Asn—DiMeTzl—p-AMF—Gly—Asp—Cys—OH wherein DiMeTzl is dimethylthioproline and p-AMF is para-aminomethyl phenylalanine is described in EP 0 422 937 and will hereafter be referred to as Compound C.

The compound referred to as Compound 16-9 described in EP 0 540 334 A1 is also a potent inhibitor of platelet aggregation. Compound 16-9 in EP 0 540 334 A1 is 1-H-isoindole-5-carboxamide, 2,3 dihydro-N-[3-(2(S)-n-butylsulfonylamino)propionic acid]-2-[2-(4-piperidinyl)ethyl]-3-oxo and will hereafter be referred to as Compound D.

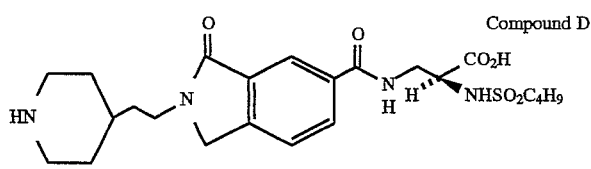

Compound D

Another inhibitor of platelet aggregation is 5-[2-(Piperidin-4-yl)ethyl]thieno[2,3-b]thiophene-2-N-[3-2(S)-(3-pyridylsulfonylamino) propionic acid] carboxamide which will hereafter be referred to as Compound E. The synthesis of Compound E is described in Scheme 5.

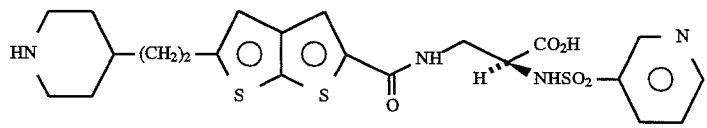

Compound E

The instant invention provides a means of identifying GP IIb/IIIa inhibitors which bind to "activated" or "unactivated" platelets. The identification of GP IIb/IIIa inhibitors which selectively bind to activated platelets is important for several reasons. Platelets circulate in the blood and thus pass through the spleen and liver, as well as other organs. Aged platelets or damaged platelets are removed by the spleen and possibly the liver. If platelets contain a foreign substance on their surface, they are often cleared by normal clearance mechanisms, or they can cause the induction of antiplatelet antibodies that recognize the platelets containing the foreign substance. In a particular subset of individuals, drugs that bind to circulating platelets cause thrombocytopenia.

Glycoprotein IIb/IIIa is a platelet protein complex, held within the platelet membrane. GPIIb/IIIa represents an antithrombotic target since it plays a critical role in platelet aggregation, which is itself involved in thrombosis. Small molecules that bind to this protein complex and prevent fibrinogen binding may thus be expected to have efficacy. Platelets normally exist in at least two forms, an activated form capable of aggregating, and a circulating form incapable of aggregating. This activating process is irreversible. Among the changes that occur during this activation process is a conversion of GPIIb/IIIa from the "inactive" to the "active" form. An ideal antithrombotic agent would therefore only bind to the "active" form, i.e., the activated platelet. This would limit drag binding to the irreversibly activated platelet. Thus, the potential for thrombocytopenia would be minimized because the majority of circulating platelets would not carry drug on their surface.

The fluorescent probe compounds of the present invention can also be used as a diagnostic for monitoring plasma drug levels and for monitoring receptor occupancy on platelets. More particularly, the fluorescent probes are useful for monitoring the interaction of inhibitors of GP IIb/IIIa with either purified GP IIb/IIIa or human platelets. A fluorescent compound is added to a sample of blood containing an amount of nonfluorescent inhibitor. The amount of fluorescence is then determined using, for example, a fluorometer, a fluorescence plate reader or a cell scanner with fluorescence detection. From the fluroescence obtained, the amount of nonfluorescent compound in the blood is estimated allowing for more appropriate dose selection; thus, the risk of bleeding which can result from too high a dosage is reduced by careful monitoring using the fluorescent probes of the present invention.

The compounds of the present invention can be prepared readily according to the following reaction schemes and examples or modifications thereof using readily available starting materials, reagents and conventional synthesis procedures. In these reactions, it is also possible to make use of variants which are themselves known to those of ordinary skill in this art, but are not mentioned in greater detail.

The term "alkyl" shall mean straight or branched chain alkanes.

The term "aryl" shall mean phenyl or naphthyl.

The term "antiplatelet agent," as used herein, shall mean any compound which interferes with the binding of fibrinogen to blood platelets. Thus, fibrinogen receptor antagonists, also known as GP IIb/IIIa inhibitors, are antiplatelet agents for purposes of the instant invention.

The term "thrombotic condition," as used herein, shall mean any condition wherein the formation, development or presence of a thrombus is involved. Examples of such conditions include, but are not limited to, unstable angina, abrupt reclosure during angioplasty (PTCA), myocardial infarction, thrombotic stroke, thrombosis on stents, valves and other vascular devices, and deep vein thrombosis.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of compounds of the present invention. Those skilled in the art will readily understand that known variations of the conditions and processes of the following preparative procedures can be used to prepare these compounds. All temperatures are degrees Celsius unless noted otherwise.

Abbreviations used in the examples are as follows:

TEA or Et₃N=triethylamine

DIEA=diisopropylethylamine

BOP=benzotriazol-1-yloxytris(dimethyl-aminophosphonium hexafluorophosphate

NMM=N-methylmorpholine

DMF=dimethylformamide

TFA=trifluoroacetic acid

THF=tetrahydrofuran

BOC or Boc=tert-butyloxycarbonyl

Cbz=benzyloxycarbonyl

NBS=N-bromosuccinimide

DMSO=Dimethylsulfoxide

EtOAc=ethyl acetate

EtOH=ethanol

MeOH=methanol

HOAc=acetic acid

CHCl₃=chloroform
CH₃CN=acetonitrile
CH₂Cl₂=methylene chloride

SCHEME 1

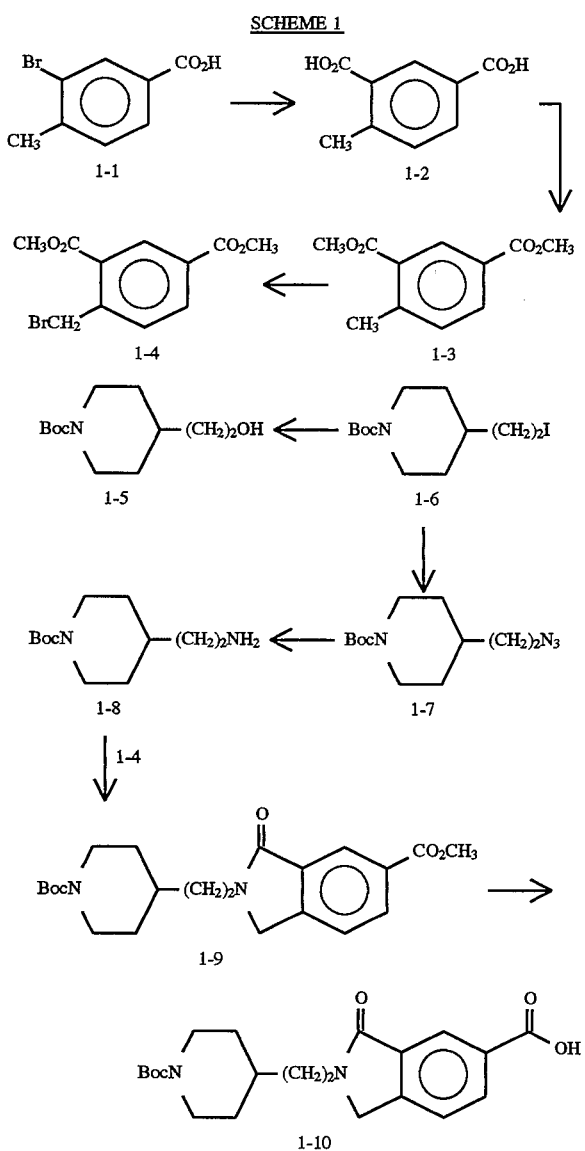

EXAMPLE 1

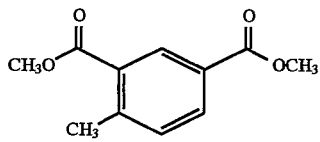

Dimethyl 4-methylbenzene-1,3-dicarboxylate (1-3)

A solution of 1—1 (Lancaster) (25 g, 0.116 mol) in THF (400 mL) was cooled to 0° C. and treated with methyl magnesium chloride (40 mL, 0.127 mol). The solution was then cooled to −60° C. and treated with n-butyl lithium (115 mL, 0.243 mol), maintaining the temperature of the reaction at −60° C. The greenish, opaque solution was added to a slurry of crushed dry ice and THF and stirred vigorously. After warming to room temperature, the mixture was concentrated, dissolved in water (1.5 L) and extracted three times with a 1:10 mixture of THF and EtOAc (400 mL). The EtOAc layer was concentrated to give a white solid that was suspended in hexanes, filtered, washed with hexanes and dried to give 1-2 as an amorphous white solid. R$_f$(97:3:1) CHCl₃/MeOH/HOAc)0.12. ¹H NMR (400 MHz, CD₃OD) δ8.54 (s, 1H), 8.03 (d, J=6 Hz, 1H), 7.39 (d, J=6 Hz, 1H), 2.64 (s, 3H). This diacid (1-2) was suspended in MeOH (1 L) and HCl gas was bubbled through the solution for 10 min. The solution was stirred for 48 h, then evaporated to give an oil that was chromatographed in 5% EtOAc/Hexanes to give 1-3 as an amorphous solid. R$_f$(97:3:1 CHCl₃/MeOH/HOAc) 0.85. ¹H NMR (400 MHz, CDCl₃) δ8.57 (s, 1H), 8.04 (d, J=8 Hz, 1H), 7.33 (d, J=8 Hz, 1H), 3.92 (s, 6H), 2.66 (s, 3H).

EXAMPLE 2

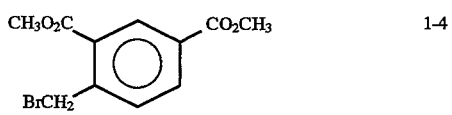

Dimethyl 4-bromomethylbenzene-1,3-dicarboxylate (1-4)

A solution of 1-3 (1.35 g, 6.5 mmole) in CHCl₃ (20 ml) was treated with dibenzoyl peroxide (0.078 g, 3.5 mmol) and N-bromosuccinimide (NBS) (1.1 g, 6.5 mmole) and the resulting solution was heated at reflux for 2 h.

The cooled reaction mixture was concentrated, taken up in CCl₄, filtered and the filtrate was concentrated to give 1-4 as a tan solid. R$_f$0.5 [silica gel, hexane (70)/EtOAc(30)]. ¹H NMR (300 MHz, CDCl₃) δ8.6 (s, 1H), 8.13 (d, J=8 Hz, 1H), 7.55 (d, J=8Hz, 1H), 4.97 (s, 2H), 3.97 (s, 3H), 3.95 (s, 3H).

EXAMPLE 3

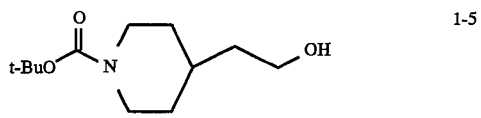

2-(4-N-t-Butyloxycarbonylpiperidine)ethanol (1-5)

4-pyridine acetic acid (50 g, 0.314 mole) was dissolved in H₂O (50 mL), and HOAc (100 mL), PtO₂ (1 g) was added and the mixture was hydrogenated at 55 psi for 72 h. An additional 1 g of PtO₂ was added after 48 h. The solution was filtered through celite, the cake was washed with H₂O and the filtrate was evaporated, using heptane to azeotrope off excess HOAc. The 4-piperidine acetic acid was obtained as a white solid. R$_f$ (9:1 EtOH/H₂O) 0.11.¹H NMR (400 MHz, CD₃OD) δ3.36 (bd, 2H), 330 (bt, 2H), 2.3 (d, J=7 Hz, 2H), 2.08 (m, 1H), 1.99 (bd, 2H), 1.47 (m, 2H). This solid was dissolved in H₂O (200 mL), and dioxane (200 mL), treated with triethylamine (76 mL, 0.546 mole), and di-t-butyldicarbonate (59.5 g, 0.273 mole) and stirred for 96 h. After 72 h, an additional equivalent of triethylamine and 10 g of di-t-butyldicarbonate was added. The organic solvent was evaporated and the remaining aqueous solution was brought to pH 10 with saturated NaHCO₃, washed with 3×50 mL EtOAc, acidified with 10% KHSO₄ to pH 2-3, extracted with 3×100 mL EtOAc, dried with MgSO₄, filtered and evaporated to give 4-(N-t-butyloxycarbonyl)piperidine acetic acid. R$_f$(9:1 EtOH/H₂O) 0.68. ¹H NMR (CDCl₃) δ4.1 (bs, 2H), 2.7 (bt, 2H), 2.27 (d, J=7 Hz, 1.95 (m, 1H), 2.7 (bd, 2H), 1.45 (s, 9H), 1.18 (m, 2H). This acid was reduced with borane to yield 2-(4-N-t-butyloxycarbonylpiperidine) ethanol, 1-5, as an oil. ¹H NMR (400 MHz, CDCl₃) δ4.08

(bd, J=12 Hz, 2H), 3.7 (t, J=6.5 Hz, 2H), 2.4 (bt, 12 Hz, 2H), 1.67 (bd, 2H), 1.6–1.45 (m, 3H), 1.45 (s, 9H), 1.12 (m, 2H).

EXAMPLE 4

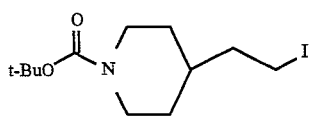

2-(4-N-t-Butyloxycarbonylpiperidine)ethyl iodide (1-6)

Boc-4-piperidine-2-ethanol (1-5) (10.42 g, 0.048 mole) was dissolved in 400 ml benzene and imidazole (4.66 g, 0.068 moles), iodine (12.1 g, 0.048mole), and triphenylphosphine (15.24 g, 0.05 moles) were added at room temperature. After 6 h, the reaction mixture was filtered and the filtrate was evaporated to give a dark residue. This was purified by flash chromatography on silica gel eluting with 10%-EtOAc-hexanes to give 1-6 as a yellow oil.

EXAMPLE 5

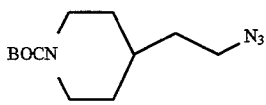

2-(4-N-t-Butyloxycarbonylpiperidine)ethylazide (1-7)

To 1-6 (27.9 g, 0.082 moles) dissolved in DMSO (400 ml) was added sodium azide (5.01 g, 0.086 moles) at room temperature and the resulting solution was heated at 65° for 2 h. The cooled reaction mixture was diluted with 250 ml EtOAc, extracted with 2×100 ml portions of water, 2×50 ml portions of brine and then dried (MgSO$_4$). Solvent removal provided 1-7 as a pale yellow oil, R$_f$ 0.5 (silica gel, 70% acetone/hexane).

EXAMPLE 6

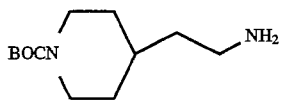

2-(4-N-t-Butyloxycarbonylpiperidine)ethylamine (1-8)

To a solution of 1-7 (19.3 g, 0.076 moles) in THF (400 ml)/H$_2$O (195 ml) was added triphenylphosphine (80.0 g, 0.305 moles) in one portion at room temperature. This was stirred at room temperature 3 h and the organic solvents were then removed in vacuo. The residue was acidified to pH 2 with 10% KHSO$_4$ solution and this was extracted 4×100 ml portions of EtOAc. The organic extract was extracted with 2×100 ml portions of 10% KHSO$_4$ and the aqueous phases were combined and the pH was adjusted to 10 with 2N NaOH. This solution was extracted with 4×200 ml portions of CH$_2$Cl$_2$. These were combined, dried (MgSO$_4$) and the solvent was removed to give 1-8 as an oil. R$_f$ 0.3 (silica gel, eluting with 10% CH$_3$OH in CHCl$_3$/NH$_3$). $^1$H NMR (300 MHz, CDCl$_3$) δ4.05 (broad, 2H), 2.72 (t, J=7.2 Hz, 2H), 2.62 (m, 2H), 1.64 (d, J=12.2 Hz, 2H), 1.43 (s, 9H), 1.42–1.32 (m, 5H), 1.09 (m, 2H).

EXAMPLE 7

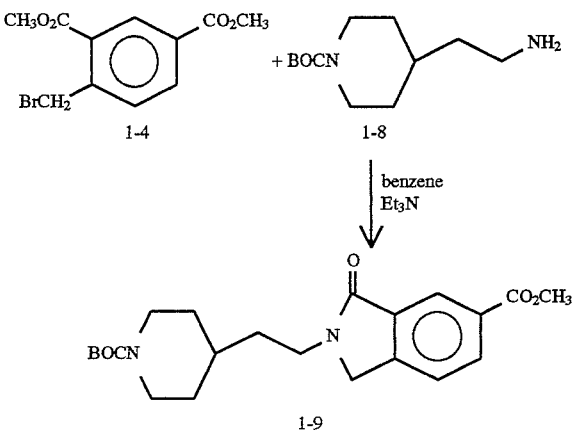

Methyl-1H-Isoindole-5-carboxylate, 2,3-dihydro-N-[2-(4-N-t-butyloxycarbonylpiperidinyl)ethyl]-3-oxo (1-9)

A solution of 1-4 (1.0 g, 3.5 mmoles) in benzene (5 ml) was treated with 1-8 (0.80 g, 3.5 mmol) and triethylamine (0.49 ml, 3.5 mmol) and the reaction mixture was heated at reflux for 3 h. The solvent was removed and the residue was taken up in EtOAc, washed in 10% KHSO4 solution, H$_2$O, brine and dried. Solvent removal gave a residue that was purified by flash chromatography on silica gel eluting with hexane (1)/EtOAc(1) to give pure 1-9. R$_f$ 0.2 (silica gel, hexane (1)/EtOAC(1)). $^1$H NMR (300 MHz, CDCl$_3$) δ1.08 (2H, m), 1.43 (9H, s), 1.61 (4H, m), 1.73 (2H, bd), 2.62 (2H, bt), 3.64 (2H, t), 3.93 (3H, s), 4.07 (2H, m), 4.40 (2H, s), 7.50 (1H, d), 8.21 (1H, dd), 8.47 (1H, d).

EXAMPLE 8

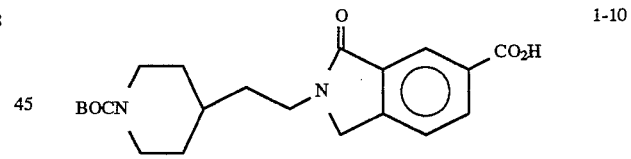

1H-Isoindole-5-carboxylic acid, 2,3-dihydro-N-[2-(4-N-t-butyloxy-carbonylpiperidinyl)ethyl]-3-oxo (1-10)

A solution of 1-9 (0.43 g, 1.12 mmole) in THF (1)/ MeOH(1)H$_2$O(1) (9 ml) was treated at room temperature with LiOH·H$_2$O (0.235 g, 5.6 mmol) and the resulting solution was stirred for 4 h. The reaction mixture was then diluted with EtOAc (75 ml)/10% KHSO$_4$ solution (30 ml) and the organic phase was separated and dried (Na$_2$SO$_4$). Solvent removal gave the desired acid 1-10. R$_f$ 0.5 (silica gel, CH$_2$Cl$_2$(9)/MeOH (0.5)/HOAc(0.5)). $^1$H NMR (300 MHz, CDCl$_3$) δ1.12 (2H, m), 1.42 (9H, s), 1.60 (3H, m), 1.71 (2H, bd), 2.63 (2H, bt), 3.68 (2H, t), 4.08 (2H, m), 4.40 (2H, s), 7.03 (1H, d), 8.28 (1H, dd), 8.60 (l H, s).

SCHEME 2

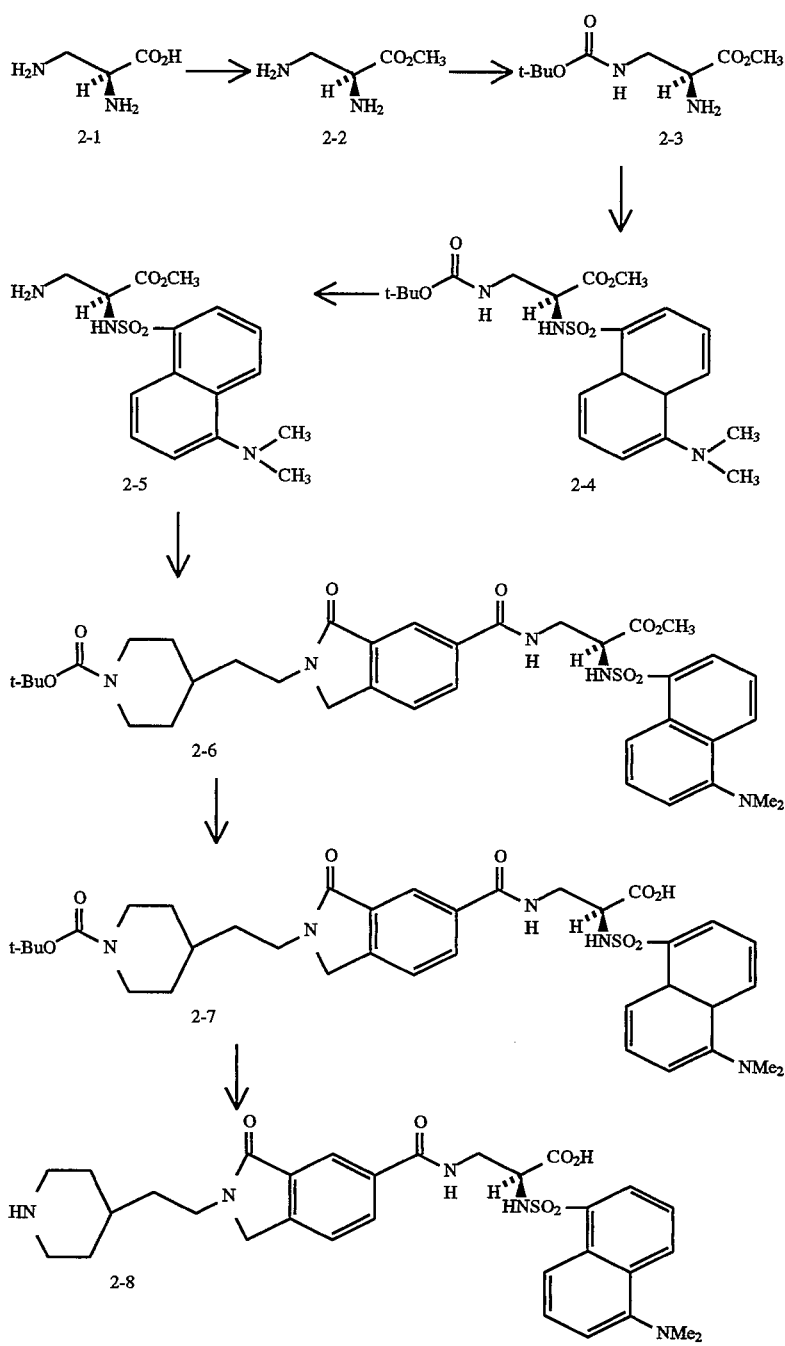

EXAMPLE 9

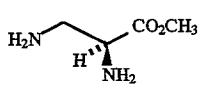

Methyl 2(S),3-diaminopropionate hydrochloride (2-2)

Methanol (400 mL) was cooled to 0° C. and thionyl chloride (217 mL, 3.0 moles, 20 eq) was added dropwise under argon. After addition was completed, the solution was warmed to RT for 20 min. 2(S),3-Diaminopropanoic acid 2-1 (20 g, 0.143 mole) (Schweizerhall Chemicals) was crushed to a fine powder and added to the solution. The reaction was heated to reflux for 48 h, at which time TLC showed a small amount of starting material remaining. An additional portion of methanol (100 mL) and thionyl chloride (72 mL) was prepared as before and added to the reaction at RT; the reaction was then stirred overnight at RT. The reaction was worked up by removal of solvent at 40° C. in vacuo to give 2-2 as foam. $R_f$ 0.72 (9:1:1 EtOH/$H_2O$/$NH_4OH$). $^1H$ NMR (400 MHz, $D_2O$) δ4.55 (dd, J=5.4 8.2 Hz, 1H), 3.92 (s, 3H), 3.64 (dd, J=8.2, 13.8 Hz, 1H), 3.55 (dd, J=5.4, 13.8 Hz, 1H).

EXAMPLE 10

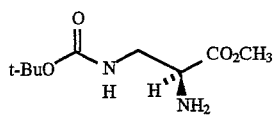

2-3

Methyl [2(S)-amino-3-(N-t-Butyloxycarbonylamino] propionate (2-3)

2-2 (6.0 g, 31.5 mmole) was crushed to a fine powder, suspended in 1L of $CH_2Cl_2$ and cooled to $-78°$ C. under argon. Triethylamine (17.5 mL, 0.126 mole, 4 eq) was added dropwise as the solution gradually became homogenous. Di-t-butyldicarbonate (6.18 g, 2.83 mmole, 0.9 eq) was dissolved in 50 mL $CH_2Cl_2$ and added dropwise to the solution. After the addition was completed, the reaction was placed in an ice bath and stirred for 1½ h. The reaction was transferred to a separatory funnel and extracted with 3×50 mL of 10% $KHSO_4$ solution. The aqueous layer was washed with 3×10 mL of $CH_2Cl_2$, then basified with sat. $NaHCO_3$ and 3N NaOH solution to pH 10 and extracted with 10×100 mL of $CH_2Cl_2$. The organic layer was dried with $Na_2SO_4$, filtered and evaporated to give of a pale yellow oil. Column chromatography on silica gel with 2.5% MeOH/EtOAc gave of pure 2-3 as an oil. $R_f$ 0.39 (5% MeOH/EtOAc). $^1$H NMR (400 MHz, $CDCl_3$) δ5.0 (bs, 1H), 3.72 (s, 3H), 3.56 (t, J=5.7 Hz, 1H), 3.46 (m, 1H), 3.23 (m, 1H), 1.55 (bs, 2H), 1.42 (s, 9H).

EXAMPLE 11

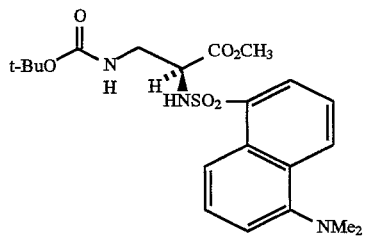

2-4

Methyl 2(S)-Dansylamino-3-(N-t-butyloxycarbonylamino)propionate (2-4)

A solution of 2-3 (0.5 g, 2.3 mmol) in $CHCl_3$ (10 mL) was treated with dansyl chloride (1.2 g, 4.6 mmol) and diisopropylethyl amine (3.6 mL, 20.7 mmol) and stirred at room temperature for 24 h. The reaction was then refluxed for 4 h, diluted with EtOAc, washed with $H_2O$ and brine, dried over $MgSO_4$, filtered and evaporated. Chromatography (30% EtOAc/Hexanes) gave 2-4 as a yellow solid. $R_f$ (30% EtOAc/Hexanes) 0.22. $^1$H NMR (300 MHz, $CDCl_3$) δ8.56 (d, 1H), 8.30 (d, 1H), 8.23 (d, 1H), 7.61 (t, 1H), 7.52 (t, 1H), 7.21 (d, 1H), 5.8 (bd, 1H), 4.8 (bs, 1H), 3.95 (m, 1H), 3.45 (m, 2H), 3.40 (s, 3H), 2.9 (s, 6H), 1.4 (s, 9H).

EXAMPLE 12

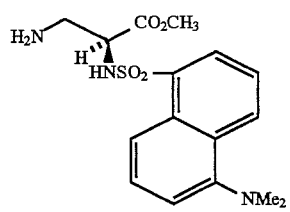

2-5

Methyl 2(S)-Dansylamino-3-aminopropionate (2-5)

A solution of 2-4 (0.43 g, 0.95 mmol) was suspended in EtOAc (15 mL) and cooled to $-78°$ C. HCl gas was bubbled through the solution and the solution became homogenous. The solution was placed in an ice bath for 0.5 h, then concentrated to give 2-5 as an amorphous yellow solid. $^1$H NMR (300 MHz, $CD_3OD$) δ8.97 (d, 1H), 8.62 (d, 1H), 8.44 (d, 1H), 8.18 (d, 1H), 7.95 (t, 2H), 4.25 (dd, 1H), 3.52 (s, 6H), 3.35 (dd, 1H), 3.12 (dd, 1H), 3.06 (s, 3H).

EXAMPLE 13

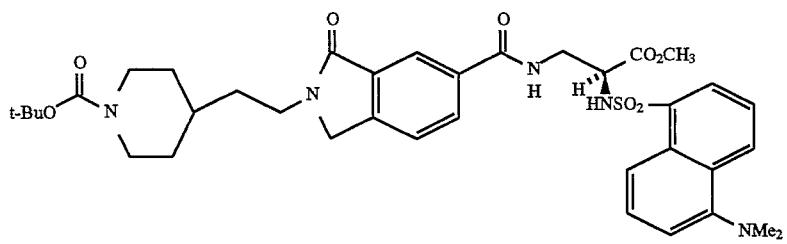

2-6

1H-Isoindole-5-carboxamide, 2,3-dihydro-N-[methyl 2(S)-dansylamino-3-aminopropionate]-2-[2-(4-N-t-butyloxycarbonylpiperidinyl)ethyl]-3-oxo (2-6)

A solution of 1-10 (0.25 g, 0.65 mmol) and 2-5 (0.37 g, 0.975 mmol) in acetonitrile (5 mL) was treated with N-methyl morpholine (0.18 mL, 1.62 mmol) and BOP reagent (0.428 g, 0.975 mmol) at room temperature for 24 h. The reaction mixture was diluted with EtOAc and washed with 10% $KHSO_4$, $H_2O$ and brine. The organic layer was dried ($MgSO_4$) filtered and evaporated. Chromatography (EtOAc) gave 2-6 as a bright green solid. $R_f$ (EtOAc) 0.21. $^1$H NMR (300 MHz, CDCl$_3$) δ8.5 (d, 1H), 8.31 (d, 1H), 8.24 (d, 1H), 8.07 (s, 1H), 7.96 (d, 1H), 7.6–7.45 (m, 3H), 7.15 (d, 1H), 7.03 (t, 1H), 6.4 (d, 1H), 4.4 (s, 2H), 4.1 (m, 3H), 3.9–3.6 (m, 4H), 3.45 (s, 3H), 2.88 (s, 6H), 2.7 (bt, 2H), 1.76 (bd, 3H), 1.7–1.6 (m, 2H), 1.4 (s, 9H), 1.2 (m, 2H).

EXAMPLE 14

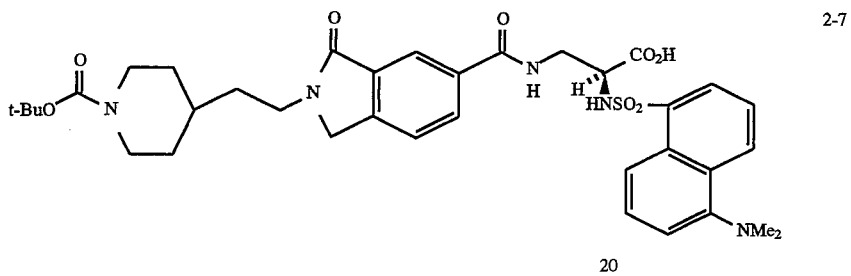

2-7

1H-Isoindole-5-carboxamide, 2,3-dihydro-N-[2-(S)-dansylamino-3-aminopropionic acid]-2-[2-(4-N-t-butyloxycarbonylpiperidinyl)ethyl]-3-oxo (2-7)

A solution of 2-6 (0.33 g, 0.46 mmol) was dissolved in a 1:1:1 mixture of THF, H$_2$O and MeOH (6 mL) and treated with LiOH·H$_2$O (0.096 g, 2.3 mmol) for 24 h. The reaction was acidified with 10% KHSO$_4$ and extracted with EtOAc, the EtOAc layer was dried (MgSO$_4$) filtered and evaporated to give 2-7 as a yellow solid. $R_f$ (9:1:1 CH$_2$Cl$_2$/MeOH/HOAc) 0.31. $^1$H NMR (300 MHz, CD$_3$OD) δ8.5 (d, 1H), 8.35 (d, 1H), 8.21 (d, 1H), 7.78 (s, 1H), 7.72 (d, 1H), 7.55 (m, 3H), 4.55 (s, 2H), 4.21 (dd, 1H), 4.05 (bd, 2H), 3.7 (m, 3H), 3.51 (dd, 1H), 2.96 (s, 6H), 2.74 (bt, 2H), 1.8 (bd, 2H), 1.7–1.6 (m, 2H), 1.45 (s, 9H), 1.14 (m, 2H).

EXAMPLE 15

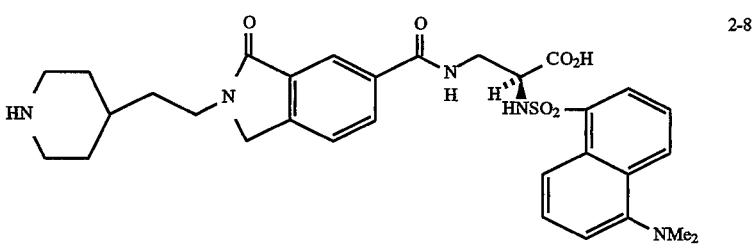

2-8

1H-Isoindole-5-carboxamide, 2,3-dihydro-N-[2(S)-dansylamino-3-aminopropionic acid]-2-[2-(4-piperidinyl)ethyl]-3-oxo (2-8)

A slurry of 2-7 (0.15 g, 0.22 mmol) in EtOAc was cooled to −78° C. and treated with HCl gas. The solution was warmed to 0° C. for 1 h, then concentrated. Chromatography (10:1:1 EtOH/H$_2$O/NH$_4$OH) gave 2-8 as an amorphous bright yellow solid. $^1$H NMR (400 MHz, D$_2$O) δ8.01 (d, 1H), 7.96 (d, 1H), 7.86 (d, 1H), 7.32 (t, 1H), 7.23 (t, 1H), 7.17 (d, 1H), 7.07 (d, 1H), 7.01 (s, 1H), 6.55 (d, 1H), 4.31 (s, 2H), 3.74 (dd, 1H), 3.5 (m, 2H), 3.38 (dd, 1H), 3.29 (bd, 2H), 3.23 (dd, 1H), 2.3 (bt, 2H), 1.78 (bd, 2H), 1.56 (m, 2H), 1.48 (m, 1H), 1.32 (m, 2H).

SCHEME 3

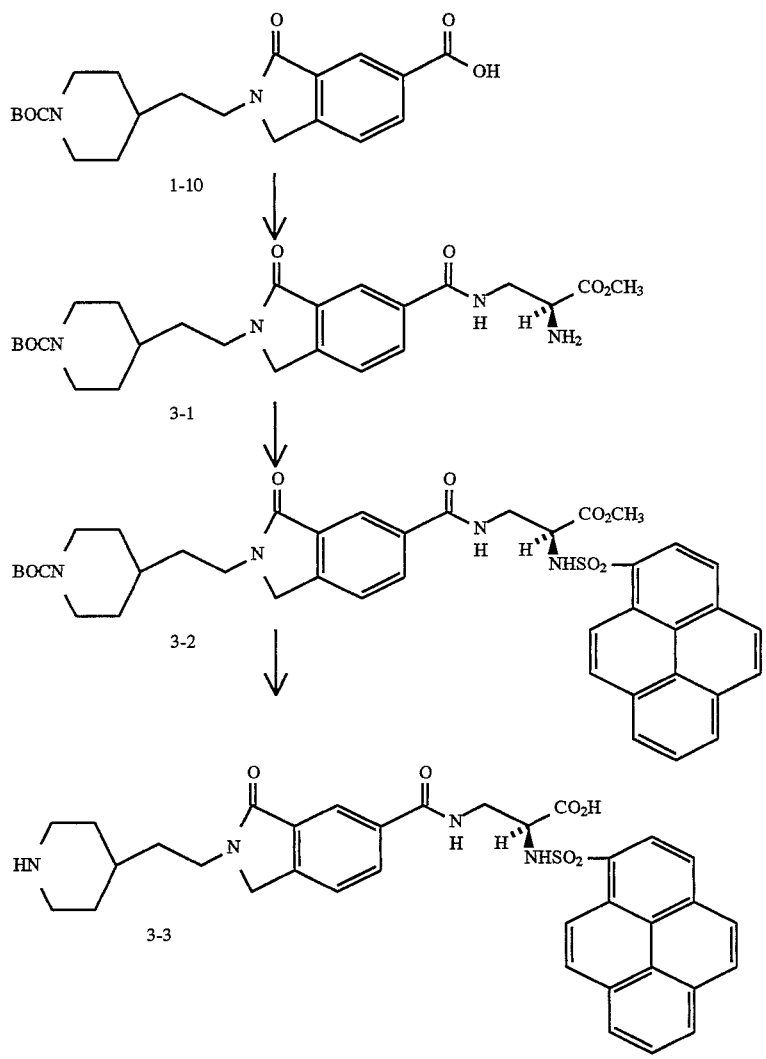

EXAMPLE 16

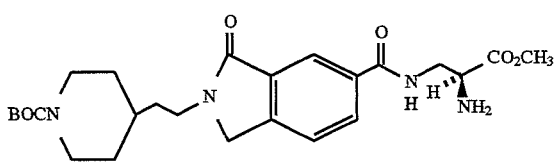

1H-Isoindole-5-carboxamide, 2,3-dihydro-N-[Methyl 2(S)-amino-3-aminopropionate]-2-[2-(4-N-t-butyloxycarbonylpiperidinyl)-ethyl]-3-oxo (3-1)

A solution of 1-10 (1 g, 2.6 mmol) in DMF (15 mL) was treated with carbonyl diimidazole (0.42 g, 2.6 mmol) for 2 h. This solution was added dropwise to a solution of 2-2 (0.915 g, 5.2 mmol), N-methyl morpholine (1.7 mL, 15.6 mmol) in DMF (15 mL) and the mixture was stirred 48 h. The solution was diluted with EtOAc and 10% $KHSO_4$ and the layers separated. The organic layer was extracted once more with 10% $KHSO_4$, then the combined aqueous extracts were brought to pH 10 with sat. $NaHCO_3$ and extracted with EtOAc and $CH_2Cl_2$. These organic layers were combined and concentrated to give crude 3-1 which was used without further purification. $^1$H NMR (400 MHz, $CD_3OD$) δ8.17 (s, 1H), 8.06 (d, 1H), 7.96 (s, 1H), 7.68 (d, 1H), 7.05 (s, 1H), 4.62 (bs, 2H), 4.56 (s, 2H), 4.04 (bd, 2H), 3.72 (s, 3H), 3.71–3.65 (m, 4H), 2.7 (bs, 2H), 1.8 (bd, 2H), 1.64 (m, 2H), 1.5 (m, 1H), 1.45 (s, 9H), 1.12 (m, 2H).

EXAMPLE 17

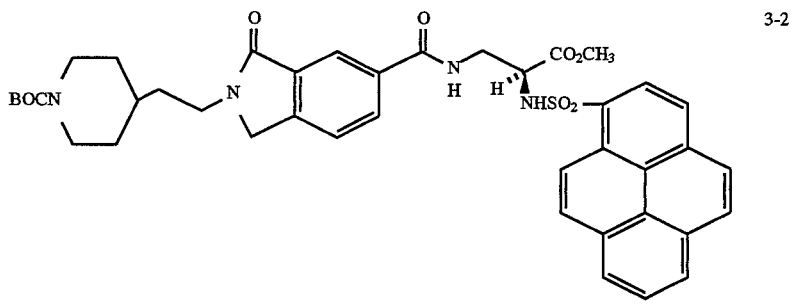

H-lsoindole-5-carboxamide, 2,3-dihydro-N-[methyl-
2(S)-(1-pyrenesulfonyl)amino-3-aminopropionate]-
2-[2-(4-N-t-butyloxycarbonylpiperidinyl)ethyl]-3-
oxo (3-2)

A solution of 3-1 (0.05 g, 0.1 mmol) in $CH_3CN$ was treated with 1-pyrenesulfonylchloride (Molecular Probes, Inc.) (0.03 g, 0.1 mmol) and pyridine (0.008 mL, 0.1 mmol) and stirred for 24 h. The solution was diluted with EtOAc and washed with $H_2O$, 10% $KHSO_4$, and brine, dried over $MgSO_4$, filtered and concentrated. Chromatography (70% EtOAc) gave 3-2 as an off-white solid. $^1H$ NMR (400 MHz, $CDCl_3$) δ8.93 (d, 1H), 8.66 (d, 1H), 8.3–8.0 (m, 7H), 7.62 (s, 1H), 7.45 (d, 1H), 6.98 (d, 1H), 6.46 (t, 1H), 6.22 (d, 1H), 4.2–4.0 (m, 5H), 3.7–3.6 (m, 3H), 3.24 (s, 3H), 2.64 (m, 2H), 1.78 (d, H), 1.64 (m, 2H), 1.43 (s, 9H), 1.2 (m, 2H).

EXAMPLE 18

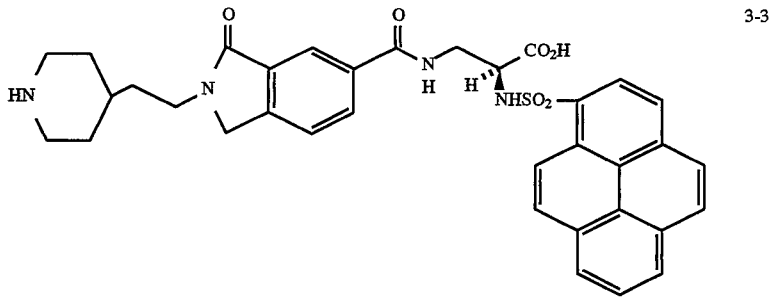

1H-Isoindole-5-carboxamide, 2,3-dihydro-N-
[methyl-2(S)-(1-pyrene-sulfonyl)amino-3-
aminopropionic acid]-2-[2-(4-N-t-butyloxycarbonyl-
piperidinyl)ethyl]-3-oxo (3-3)

A solution of 3-2 (0.12 g, 0.152 mmol) in dioxane (5 mL) was treated with 6N HCl (10 mL) for 24 h. The reaction was then heated to 50° C. for 1 h and concentrated to give 3-3 as an amorphous white solid. $^1H$ NMR (400 MHz, $CD_3OD$) δ8.84 (d, 1H), 8.59 (d, 1H), 8.2–8.1 (m, 4H), 8.03 (d, 1H), 7.96 (m, 2H), 7.02 (s, 1H), 6.83 (d, 1H), 6.5 (d, 1H), 4.31 (dd, 1H), 4.03 (dd, 2H), 3.7–3.5 (m, 3H), 3.38 (m, 3H), 2.94 (bt, 2H), 2.09 (bs, 2H), 1.7 (m, 2H), 1.6 (m, 1H), 1.45 (m, 2H).

SCHEME 4
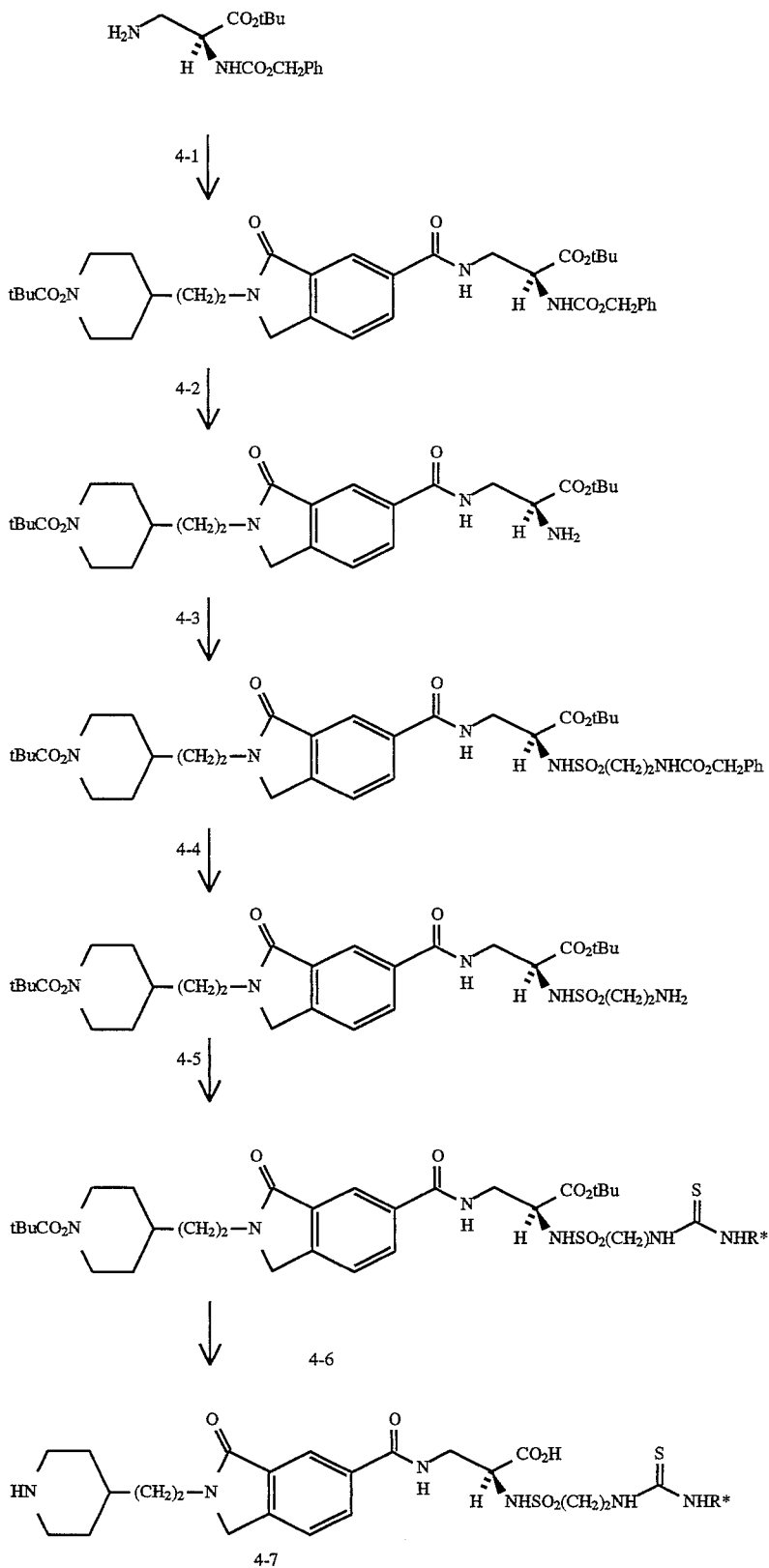

-continued
SCHEME 4

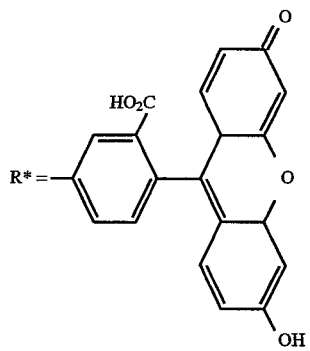

EXAMPLE 19

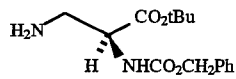

t-Butyl 2-(benzyloxycarbonyl)amino-3-aminopropionate (4-1)

A solution of 2-(S)-(benzyloxycarbonyl)amino-3-aminopropionate (Fluka) (5.25 g, 22 mmol) in dioxane (75 mL) and conc. sulfuric acid (9 mL) was cooled to 0° C. and treated with 100 mL isobutylene in a Fisher Porter high pressure apparatus. The reaction was allowed to warm to room temperature and was stirred for 24 h. The reaction was vented, then poured into water (200 mL) to give an acidic solution that was extracted with ether (2×50 mL). The aqueous layer was carefully basified with conc. NaOH to pH 11-12 and extracted with 3×150 mL EtOAc. The EtOAc was removed in vacuo and the residue was azeotroped with toluene and dried under vacuum to give 4-1 as an oil. $R_f$ (5% MeOH/CHCl$_3$ saturated with NH3) 0.31. $^1$H NMR (400 MHz, CDCl$_3$) δ7.3 (m, 5H), 5.6 (bs, 1H), 5.1 (s, 2H), 4.22 (bs, 1H), 3.05 (m, 2H), 1.45 (s, 9H), 1.4–1.2 (b, 2H).

EXAMPLE 20

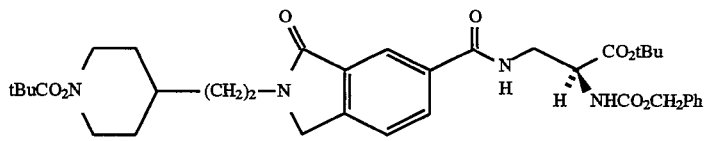

1-H-Isoindole-5-carboxamide, 2,3-dihydro-N-[t-butyl(benzyloxy-carbonyl)-2(S)-amino-3-propionate]-2-[2-(4-N-t-butyloxycarbonyl-piperidinyl)ethyl]-3-oxo (4-2)

A solution of 1-10 (1 g, 2.57 mmol) in DMF (15 mL) was treated with 4-1 (0.83 g, 2.8 mmol), BOP reagent (1.7 g, 3.8 mmol) and NMM (0.85 mL) and stirred for 24 h. The DMF was removed in vacuo and the residue was dissolved in EtOAc and washed successively with 10% KHSO$_4$, water, saturated NaHCO$_3$, water, and brine. The solution was dried over MgSO$_4$, filtered and evaporated. Column chromatography (20% Hexanes/EtOAc) gave 4-2 as a white foam. $R_f$ (20% Hexanes/EtOAc) 0.25. $^1$H NMR (400 MHz, CDCl$_3$) δ8.15 (s, 1H), 8.05 (d, 1H), 7.5 (d, 1H), 1.3 (m, 5H), 7.0 (s, 1H), 5.8 (bs, 1H), 5.15 (s, 2H), 4.42 (m, 1H), 4.4 (s, 2H), 4.1 (m, 2H), 3.85 (m, 2H), 3.7 (t, 2H), 2.65 (bt, 2H), 1.75 (d, 2H), 1.6 (m, 2H), 1.45 (s, 19H), 1.2 (m, 2H).

EXAMPLE 21

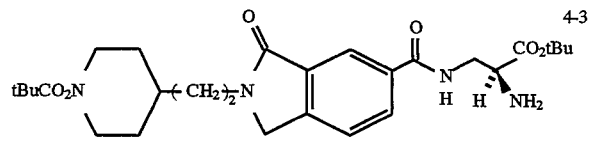

1-H-Isoindole-5-carboxamide, 2,3-dihydro-N-[t-butyl 2(S)-amino-3-propionate]-2-[2-(4-N-t-butyloxycarbonylpiperidinyl)ethyl]-3-oxo (4-3)

A solution of 4-2 (1.5 g, 2.25 mmol) in EtOH was treated with 10% Pd/C and hydrogen gas under balloon pressure for 2 h, then filtered through Solka-Floc and evaporated to give

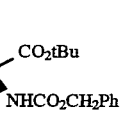

4-3 as a grey-brown foam. $R_f$ (5% MeOH/CHCl$_3$ saturated with NH$_3$) 0.24. $^1$H NMR (400 MHz, CDCl$_3$) δ8.15 (s, 1H), 8.1 (d, 1H), 7.5 (d, 1H), 6.95 (bs, 1H), 4.4 (s, 2H), 4.1 (m, 2H), 3.85 (m, 1H), 3.7 (m, 2H), 3.6 (dd, 1H), 3.45 (dd, 1H), 2.7 (bt, 2H), 75 (d, 2H), 1.45 (s, 9H), 1.44 (s, 9H), 1.15 (m, 2H).

EXAMPLE 22

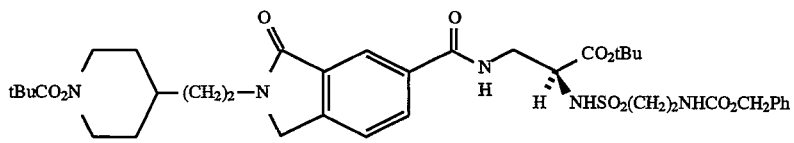

1-H-Isoindole-5-carboxamide, 2,3-dihydro-N-[t-butyl [2-benzyloxy-carbonylaminoethyl]sulfonyl-2(S)-amino-3-propionate]-2-[2-(4-N-t-butyloxycarbonylpiperidinyl)ethyl]-3-oxo (4-4)

A solution of 4-3 (0.503 g, 0.95 mmol) in CHCl₃ (20 mL) was cooled to 0° C. and treated with 2-(benzyloxycarbonylamino)-ethylsulfonyl chloride (Bricas, et al., *Biochemica et Biophysica Acta*, 1955 (18) 358) (0.525 g, 1.9 mmol) and NMM (0.6 mL, 5.7 mmol). After stirring for 2 h, the solution was diluted with CHCl₃, washed with 10% KHSO₄, brine, dried over MgSO₄, filtered and evaporated. Column chromatography (20% Hexanes/EtOAc) gave 4-4. $R_f$ (20% Hexanes/EtOAc) 0.22. ¹H NMR (400 MHz, CDCl₃) δ8.18 (s, 1H), 8.05 (d, 1H), 7.5 (d, 1H), 7.3 (m, 5H), 6.9 (bs, 1H), 5.8 (d, 1H), 5.58 (ms, 1H), 5.1 (s, 2H), 4.4 (s, 2H), 4.25 (m, 1H), 4.1 (m, 2H), 3.85 (m, 2H), 3.7 (m, 4H), 3.25 (m, 2H), 2.65 (m, 2H), 1.75 (d, 2H), 1.6 (m, 2H) 1.46 (s, 9H), 1.44 (s, 9H), 1.15 (m, 2H).

EXAMPLE 23

1-H-Isoindole-5-carboxamide, 2,3-dihydro-N-[t-butyl [(5-fluoresceinyl-aminothiocarbonyl)-2-aminoethylsulfonyl]-2(S)-amino-3-propionate]-2-[2-(4-N-t-butyloxycarbonylpiperidinyl)ethyl]-3-oxo (4-6)

A solution of 4-5. (0.15 g, 0.23 mmol) in DMF (10 mL) was treated with Fluorescein isothiocyanate (isomer 1, Aldrich) (92 mg, 0.23 mmol) and NMM (0.15 mL, 1.4 mmol). After 2 h, the solvent was removed in vacuo and the residue was chromatographed (30% MeOH/CHCl₃+2% conc. NH₄OH) to give 4-6 as a bright orange solid. $R_f$ (30% MeOH/CHCl₃+2% conc. NH₄OH) 0.21. ¹H NMR (400 MHz, CD₃OD) δ8.18 (s, 1H), 8.08 (d, 1H), 7.92 (s, 1H), 7.4 (dd, 1H), 7.62 (d, 1H), 7.38 (d, 1H), 6.98 (m, 2H), 6.65 (s, 1H), 6.6 (dd, 2H), 4.5 (s, 2H), 4.32 (dd, 1H), 4.1–4.0 (m, 4H), 3.6 (dd, 1H), 3.65 (m, 3H), 3.49 (m, 1H), 3.48 (m, 1H), 2.4 (m, 2H), 1.75 (bd, 2H), 1.65 (m, 2H), 1.48 (s, 9H), 1.46 (s, 9H), 1.15 (m, 2H).

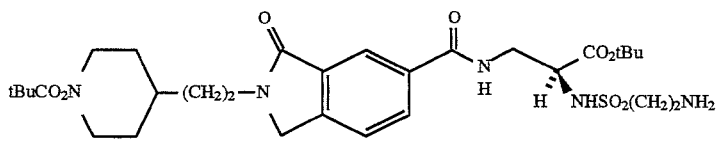

4-5

1-H-Isoindole-5-carboxamide, 2,3-dihydro-N-[t-butyl [2-aminoethyl-sulfonyl]-2(S)-amino-3-propionate]-2-[2-(4-N-t-butyloxycarbonyl-piperidinyl)ethyl]-3-oxo (4-5)

A solution of 4-4 (220 mg, 0.28 mmol) in EtOH (20 mL) and water (5 mL) was treated with 85 mg of 10% Pd/C and hydrogen gas at 65 psi in a Parr apparatus for 7 h. The reaction was filtered and evaporated to give 4-5 as a grey oil. $R_f$ (10% MeOH/CHCl₃) 0.24. ¹H NMR (400 MHz, CDCl₃) δ8.22 (s, 1H), 8.1 (d, 1H), 7.8 (bs, 1H), 7.5 (m, 1H), 4.4 (s, 2H), 4.1 (m, 2H), 3.9 (m, 1H), 3.7–3.5 (m, 4H), 3.4 (m, 4H), 2.6 (m, 2H), 1.75 (d, 2H), 1.6 (m, 2H), 1.48 (s, 9H), 1.46 (s, 9H), 1.2 (m, 2H).

EXAMPLE 24

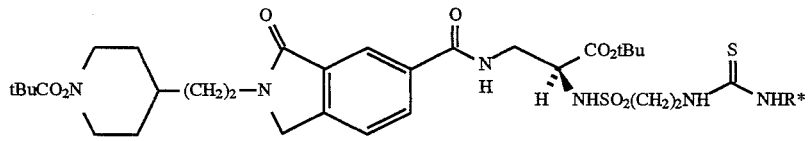

4-6

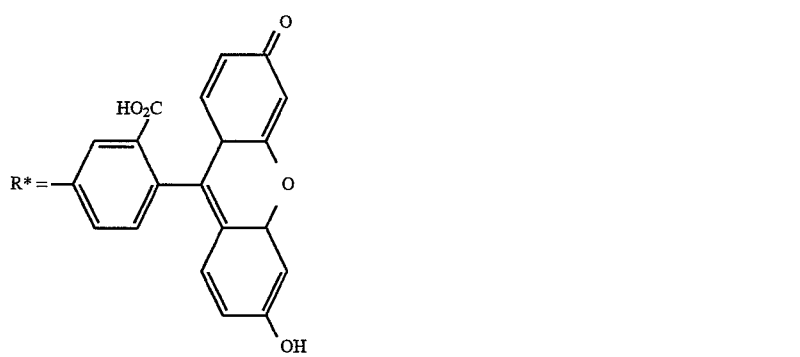

EXAMPLE 25

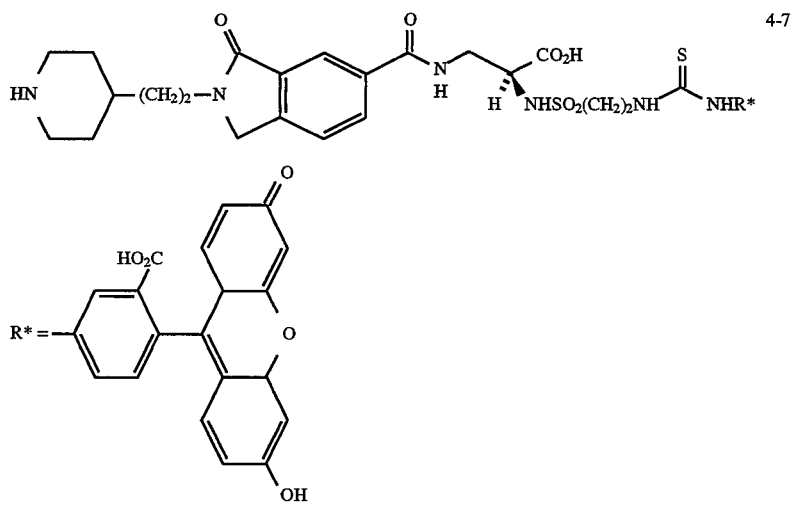

1-H-Isoindole-5-carboxamide, 2,3-dihydro-N-[[(5-fluoresceinylamino-thiocarbonyl)-2-aminoethylsulfonyl]-2(S)-amino-3-propionate]-2-[2-(4-piperidinyl)ethyl]-3-oxo (4-7)

A suspension of 4-6 (0.1 g, 0.0975 mmol) in CHCl₃ (5 mL) was cooled to 0° C. and treated with trifluoroacetic acid (5 ml) and allowed to warm to room temperature for 5 h. The solution was evaporated and the residue was purified by column chromatography (9:1:1 EtOH/H₂O/NH₄OH) and preparative HPLC to give the TFA salt 4-7 as an orange solid. $R_f$ (9:1:1 EtOH/H$_2$O/NH$_4$OH) 0.29. $^1$H NMR (400 MHz, 2/1 D$_2$O:CD$_3$CN) δ8.33 (s, 1H), 8.25 (m, 2H), 7.95 (dd, 1H), 7.88 (d, 1H), 7.4 (d, 1H), 7.05–7.0 (m, 3H), 6.88 (m, 2H), 4.65 (3H, buried), 4.25 (bt, 2H), 4.15 (dd, 1H), 3.9–3.8 (m, 4H), 3.7 (m, 2H), 3.6 (bd, 2H), 3.1 (bt, 2H), 2.18 (bd, 2H), 1.85 (m, 2H), 1.8 (m, 1H), 1.6 (m, 2H).

SCHEME 5

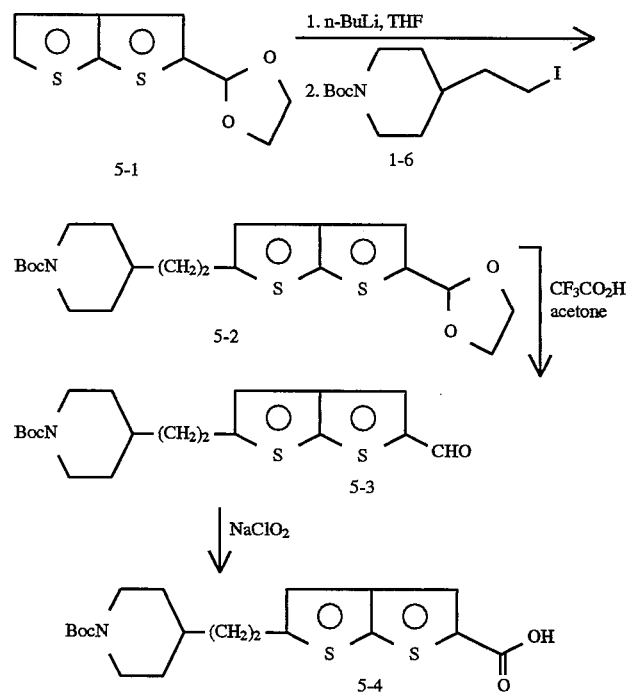

-continued
SCHEME 5

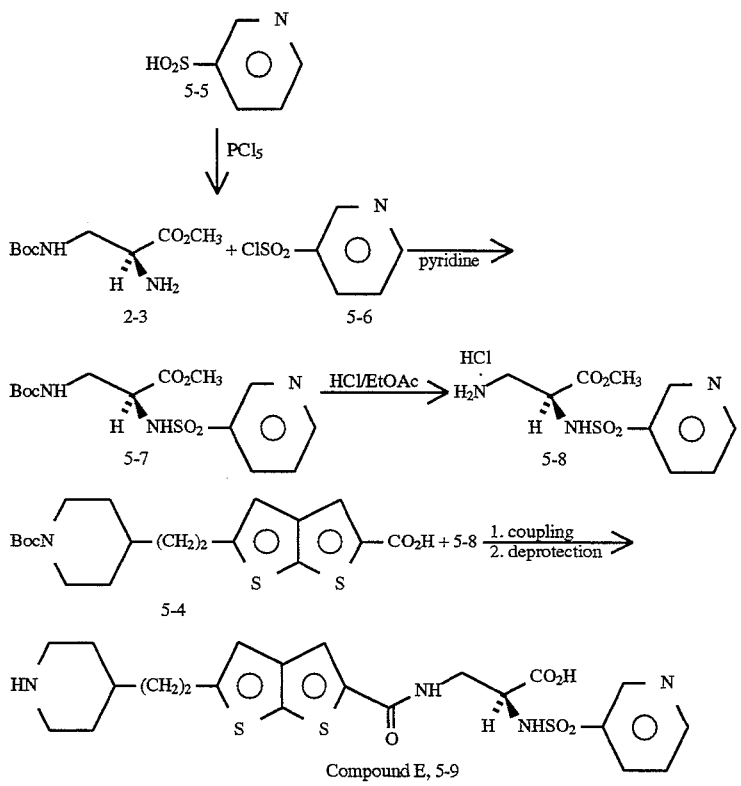

EXAMPLE 26

Preparation of 5-[2-(Piperidin-4-yl)ethyl]thieno[2,3-b]thiophene-2-N-[3-2(S)-(3-pyridylsulfonylamino)propionic acid]carboxamide (Compound E, 5-9)

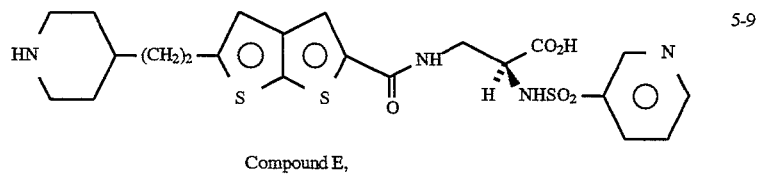

Compound E,

5-[2-(N-t-Butyloxycarbonylpiperidin-4-yl)ethyl]thieno[2,3-b]thiophene-2-carboxaldehyde ethylene glycol acetal (5-2)

5-1 (J. D. Prugh, et al. J. Med. Chem. 1991, 34, 1805–1818) (0.212 g, 1.0 mmol) was treated with n-BuLi (1.0 mmol)) with stirring for 2 h. Then, a solution of 1-6 (0.339 g) in 2 ml THF was added and the resulting solution was allowed to slowly warm to rt over 16 h. The solvent was removed and the residue quenched with ether/H$_2$O and the organic phase was separated, dried (MgSO$_4$) and concentrated. The residue was purified by flash chromatography on silica gel eluting with 10% EtOAc/hexanes to give pure 5-2. $^1$H NMR (300 MHz, CD$_3$OD) δ1.15 (2H, m), 1.45 (9H, s), 1.68 (4H, m), 2.67 (2H, t), 2.90 (2H, t), 4.10 (4H, m), 6.14 (1H, s), 6.87 (1H, s), 7.21 (1H, s).

5-[2-(N-t-Butyloxycarbonylpiperidin-4-yl)ethyl]thieno[2,3-b]thiophene-2-carboxaldehyde (5-3)

5-2 (2.36 g, 5.57 mmol) was treated with trifluoroacetic acid (6.6 ml) in acetone (60 ml) at room temp for 5 minutes, then promptly diluted with EtOAc (100 ml). This was extracted with saturated Na$_2$CO$_3$ solution (25 ml), H$_2$O, dried (MgSO$_4$) and concentrated to provide 5-3 an oil. $^1$H NMR (300 MHz, CD$_3$OD) δ1.15 (2H, m), 1.45 (9H, s), 1.68 (4H, m), 2.68 (2H, t), 2.93 (2H, t), 4.10 (2H, bd), 7.00 (1H, s), 7.77 (1H, s), 9.90 (1H, s).

5-[2-(N-t-Butyloxycarbonylpiperidin-4-yl)ethyl]thieno[2,3-b]thiophene-2-carboxylic acid (5-4)

5-3 (2.0 g, 5.27 mmol) was treated with NaClO$_2$ (5.27 g, 58.3 mmol) with stirring at room temperature for 16 h. The reaction mixture was concentrated and partitioned between EtOAc (10 ml) and 3 ml of 1N NaHSO$_4$. The organic phase was dried (MgSO$_4$), concentrated and the solvent was removed. The residue was triturated with hexane to provide 5-4. as a white solid. $^1$H NMR (300 MHz, CD$_3$OD) δ1.17 (2H, m), 1.46 (9H, s), 1.70 (4H, m), 2.68 (2H, t), 2.92 (2H, t), 4.10 (2H, bd), 6.95 (1H, s), 7.94 (1H, s).

3-Pyridylsulfonyl chloride (5-6)

3-pyridylsulfonic acid 5-5 (30 g, 0.188 mole) was added to PCl$_5$ (46.8 g, 0.225 mole) suspended in 150 mL toluene and heated to reflux overnight. The suspension was cooled and concentrated to yield a yellow oil, which was diluted with benzene, filtered through a pad of celite and concentrated to give 5-6 as a yellow oil that was used in the next step without purification. ¹H NMR (300 MHz, CDCl₃) a 9.27 (1H, s), 8.98 (1H, d, 8.35 (1H, d), 7.62 (1H, dd).

Methyl [2(S)-(3-Pyridylsulfonylamino)-3-(N-t-butyloxy-carbonyl)amino] propionate (5-7)

Methyl 2(S)-amino-3-(N-t-butyloxycarbonyl)-aminopropionate 2-3 (16.8 g, 0.077 mole) dissolved in 330 mL methylene chloride was treated with sulfonyl chloride 5-6 (20.6 g, 0.116 mole) and pyridine (12.5 mL, 0.154 mole) and the reaction was stirred for 21 hours. The reaction was concentrated, absorbed to silica and chromatographed with a gradient of 30%–70% acetone/hexanes to give crude 5-7 which was swished with hot EtOAc, cooled and filtered to give 5-7 as a pale yellow solid. RF 0.29 (30% acetone/hexanes). ¹H NMR (300 MHz, CDCl₃) δ9.0 (1H, s), 8.8 (1H, d), 8.6 (1H, d), 8.1 (1H, d), 7.45 (1H, dd), 7.3 (1H, m), 4.1 (1H, m), 4.1 (3H, s), 3.4–3.5 (2H, m), 1.4 (9H, s).

Methyl [2(S)-(3-Pyridylsulfonylamino)-3-amino] propionate (5-8)

Methyl 2(S)-(3-pyridylsulfonyl)amino-3-(N-t-butyloxycarbonyl)aminopropionate 5-7 (17.5 g, 0.049 mole) was suspended in 200 mL EtOAc and cooled to −78° C. HCl gas was bubbled through the solution for ten minutes and the solution was then placed in an ice bath. After stirring for 40 minutes at 0° C., no starting material could be detected by TLC. The solution was concentrated, first at room temperature, then at 40° C. to yield 5-8 as an off-white solid. Rf 0.34 (9:1:1 EtOH/H₂O/NH₄OH). ¹H NMR (300 MHz, CD₃OD) δ9.3 (1H, s), 9.0 (1H, dd), 8.9 (1H, d), 8.2 (1H, dd), 4.6 (1H, dd), 3.6 (3H, s), 3.5 (1H, dd), 3.3 (1H, dd).

5-[2-(Piperidin-4-yl)ethyl]thieno[2,3-b]thiophene-2-N-[3-2(S)-(3-pyridylsulfonylamino)propionic acid] carboxamide (5-7.9)

5-4 was treated as described for 2-6 with 5-8 and the resulting intermediate was deprotected as described for 2-7 and 2-8 to provide 5-9. ¹H NMR (300 MHz, D₂O) δ0.85 (2H, m), 1.07 (1H, m), 1.34 (4H, m), 2.22 (2H, t), 2.35 (2H, m), 2.38 (2H, bd), 3.06 (1H, t), 3.62 (2H, m), 6.80 (1H, s) 6.92 (1H, m), 7.24 (1H, s), 7.79 (1H, d), 7.97 (1H, dd), 8.70 (1H, d).

Using the synthetic methods described and employing commercially available sulfonylating reagents, the following examples provide further illustrative examples of the present invention:

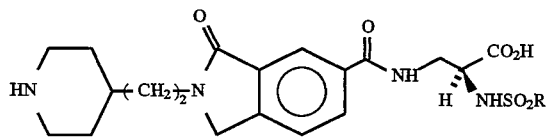

R

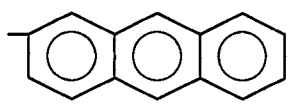

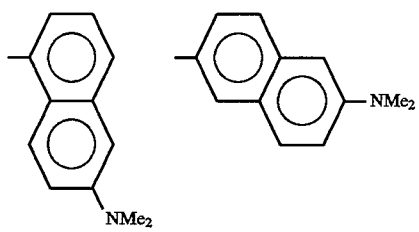

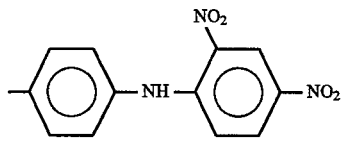

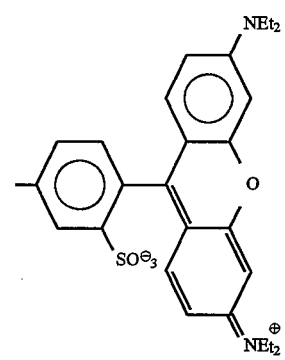

R

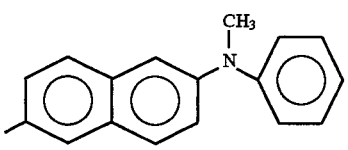

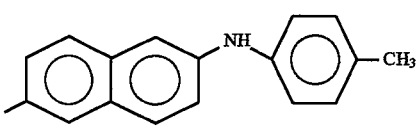

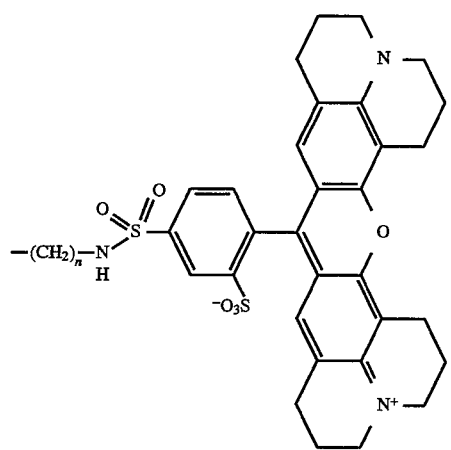

n is an integer of from 0 to 6

The sulfonyl halides are commercially available from Molecular Probes, Inc.

EXAMPLE 27

Fibrinogen Receptor Antagonist Assay

The fibrinogen receptor antagonist activity is based on evaluation of inhibition of ADP-stimulated platelets. Aggregation requires that fibrinogen bind to and occupy the fibrinogen receptor site. Inhibitors of fibrinogen binding inhibit aggregation. In the ADP-stimulated platelet aggregation assay used to determine inhibition of Compounds A through E, human platelets were isolated from fresh blood, collected into acid citrate/dextrose, by differential centrifugation, followed by gel filtration on Sepharose 2B in divalent ion-free Tyrode's buffer (pH 7.4) containing 2% bovine serum albumin.

Platelet aggregation was measured at 37° C. in a Chronolog aggregometer. The reaction mixture contained gel-filtered human platelets ($2\times10^8$ per ml), fibrinogen (100 µg/ml), $Ca^{2+}$ (1 mM), and the compound to be tested. The aggregation was initiated by adding 10 µM ADP after the other components had been added. The reaction was allowed to proceed for at least 2 minutes. The extent of inhibition of aggregation was expressed as the percentage of the rate of aggregation observed in the absence of inhibitor. The $IC_{50}$ is the dose of a particular compound inhibiting aggregation by 50% relative to a control lacking the compound. Inhibition of ADP-stimulated platelets is shown below in Table 1.

EXAMPLE 28

Use of a Fluorescent Probe to Determine the Binding Potential of Other Antiplatelet Agents

Step A: Binding Potential of Fibrinogen Receptor Antagonists to Activated Platelets The purified glycoprotein IIb/IIIa (final concentration 0.64 µM, active form which binds to RGDS affinity column) was mixed with fluorescent antagonist 2-8 (final concentration 1 µM) in a fluorescence cell and fluorescence recorded (excitation wavelength 340 nm, emission range 360–600 nm). The bound 2-8, was then displaced from GP IIb/IIIa by titration with the nonfluorescent antagonist Compound B. The fluorescence of the solution was recorded after every addition of Compound B. Change in fluorescence at wavelength 550 nm vs. final concentration of added Compound B was plotted and from such dependence (using $K_i$=3.7 nM for fluorescence antagonist 2-8), the $K_i$=4 nM for nonfluorescent antagonist Compound B toward the active form of GP IIb/IIIa was calculated.

Step B: Binding Potential of Fibrinogen Receptor Antagonists to Inactive Form of Platelets The same experiment as in Step A was carried out with the exception that, instead of active form of GP IIb/IIIa, the inactive form of GP IIb/IIIa (it does not bind to RGDS affinity column) was used. The fluorescence change vs. final concentration of Compound B was plotted to provide $K_i$=470 nM for Compound B on inactive form of GP IIb/IIIa.

The following table separates Fibrinogen receptor antagonists into two groups. Group I are those compounds whose affinity for unactivated GP IIb/IIIa is appreciably lower than the concentration necessary to inhibit platelet aggregation, and thus would not be expected to bind appreciably to unactivated platelets. Group II contains compounds whose affinity for unactivated GP IIb/IIIa is appreciably higher than the concentration necessary to inhibit platelet aggregation and thus would be expected to bind appreciably to unactivated platelets.

TABLE 1

|  | Ki (nM) (unactivated GP IIb/IIIa) | IC$_{50}$ (nM) (aggregation) |
|---|---|---|
| Group I |  |  |
| Compound A | 99 | 27 |
| Compound B | 470 | 94 |
| Compound C | 3100 | 23 |
| Group II |  |  |
| Compound D | 2.4 | 21 |
| Compound E | ≦2.7 | 8 |

While the invention has been described and illustrated with reference to certain preferred embodiments, thereof, one skilled in the art will appreciate that various changes, modifications and substitutions can be made without departing from the spirit and scope of the invention. Therefore, it will be understood that the practice of the invention encompasses all of the usual variations, adaptions, or modifications, as come within the scope of the following claims and their equivalents.

What is claimed is:

1. A fluorescent compound of the formula

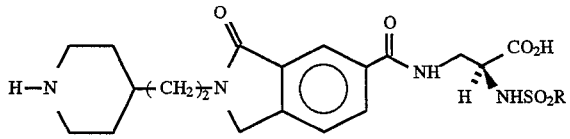

wherein

R is selected from the group consisting of $R^5$, $C_{1-6}$ alkyl substituted with $R^5$, and a mono- or fused polycylic aromatic or heteroaromatic system comprised of 6-membered aromatic or 5 to 6-membered heteroaromatic rings that are either unsubstituted or substituted with one or more of $R^1$ and $R^2$, wherein the heteroaromatic ring contains one to four heteroatoms selected from N, O or S;

$R^1$ and $R^2$ are each independently selected from
$C_{1-6}$ alkyl,
carboxyl,
hydroxyl,
azido,
nitro,
amino,
$C_{1-6}$ alkylamino,
$C_{1-6}$ dialkylamino,
arylamino,
aryl $C_{1-6}$ alkylamino,
hydroxysulfonyl or
arylazo;

aryl is a phenyl or naphthyl ring which is unsubstituted or substituted with one or more of $R^3$ and R4;

$R^3$ and $R^4$ are each independently selected from
$C_{1-6}$ alkyl,
azido,
nitro,
amino,
$C_{1-6}$ dialkylamino or
hydroxysulfonyl; and $R^5$ is

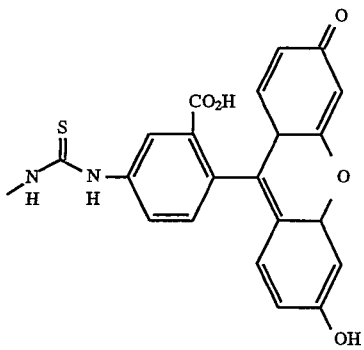

or

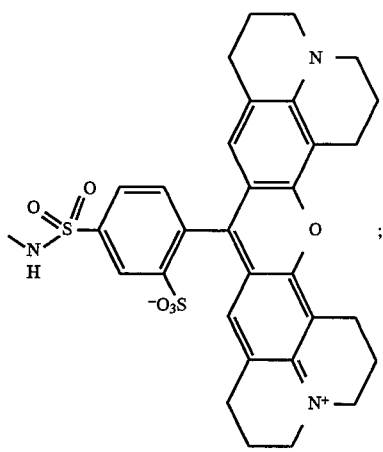

provided that when R is an unsubstituted monocyclic ring, the monocyclic ring is not phenyl or pyridyl;

and the pharmaceutically acceptable salts thereof.

2. The compound of claim 1, wherein R is selected from $C_{0-6}$ alkyl substituted with $R^5$, or a mono- or polycylic aromatic ring system that is either unsubstituted or substituted with one or more of $R^1$ and $R^2$.

3. The compound of claim 2, wherein R is selected from

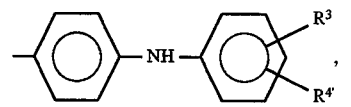

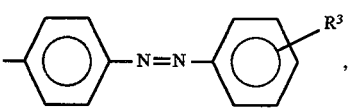

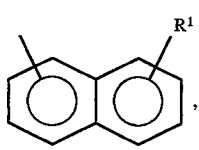

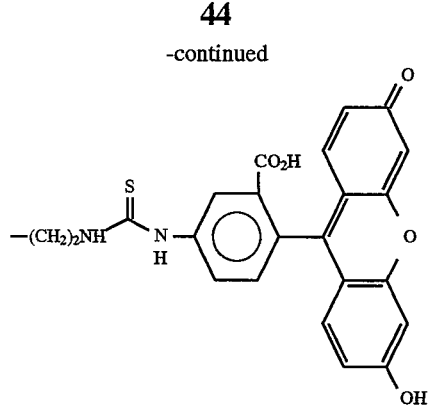

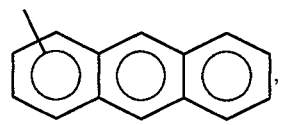

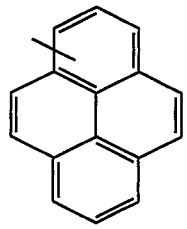

or

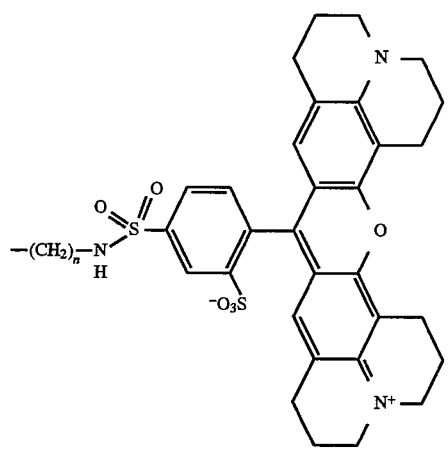

where n is an integer of from 0 to 6.

4. The compound of claim 3, wherein $R^1$ is selected from $C_{1-6}$ dialkylamino, arylamino or aryl $C_{1-6}$ alkylamino; and $R^3$ and $R^4$ are each independently selected from $C_{1-6}$ alkyl, nitro, amino or $C_{1-6}$ dialkylamino.

5. The compound of claim 4, wherein R is selected from

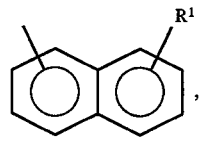

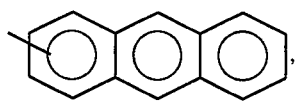

-continued

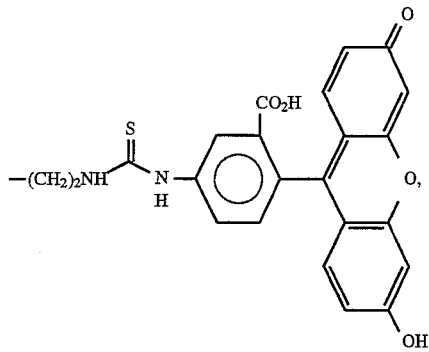

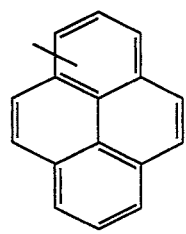

or

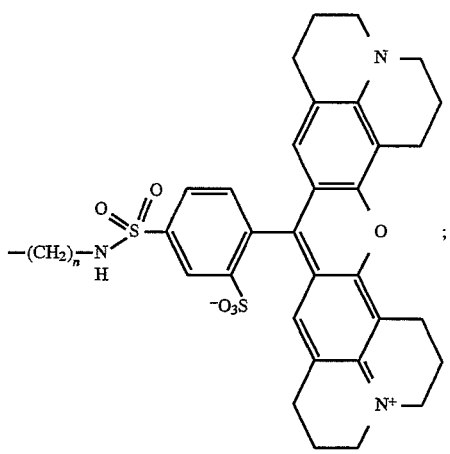

and $R^1$ is $C_{1-6}$ dialkylamino.

6. The compound of claim 5, wherein R is selected from

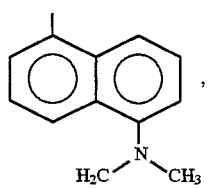

-continued

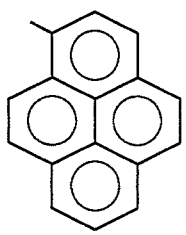

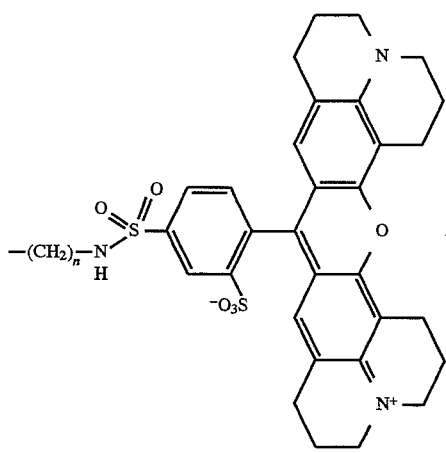

or

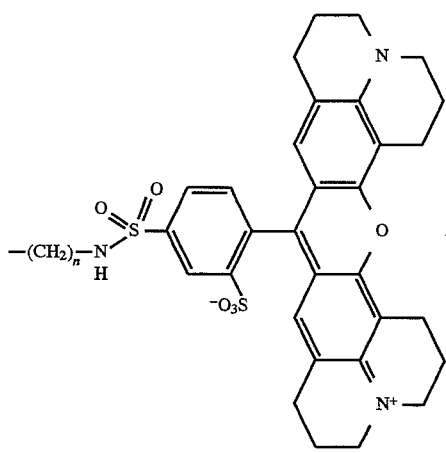

7. A method for identifying an antiplatelet agent that binds to activated platelets comprising mixing a fluorescent probe compound of claim 1 with an active form of GP IIb/IIIa receptor to bind the fluorescent probe compound to the active form of GP IIb/IIIa receptor, measuring fluorescence of fluorescent probe compound bound to GP IIb/IIIa receptor, displacing the bound fluorescent probe compound with a nonfluorescent antiolatelet agent by titrating with the nonfluorescent antiplatelet agent to form a titration solution comprising displaced probe compound and antiplatelet agent bound to the receptor, measuring fluorescence of the titration solution, determining difference in fluorescence between the fluorescence of fluorescent probe compound bound to active GP IIb/IIIa receptor and fluorescence of the titration solution, and identifying, based on a showing of difference between fluorescence of fluoerescent probe compound bound to active GP IIb/IIIa receptor and fluorescence of the titration solution, an antiplatelet agent that binds to activated platelets.

8. The method of claim 7, wherein R is selected from

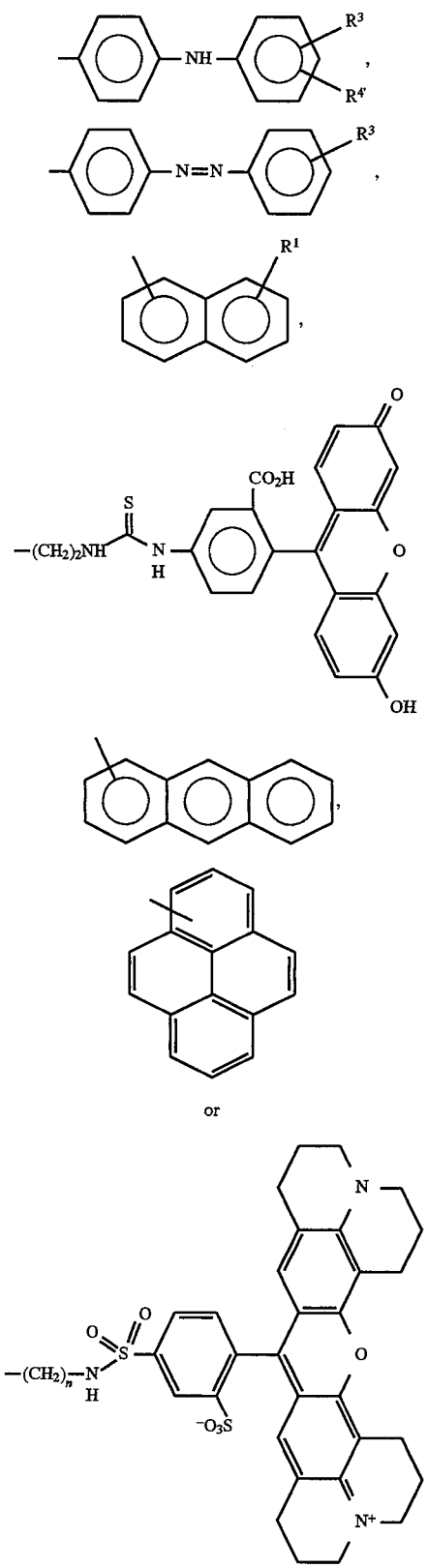

or where n is an integer of from 0 to 6.

9. The method of claim 8, wherein $R^1$ is selected from $C_{1-6}$ dialkylamino, arylamino or aryl $C_{1-6}$ alkylamino; and $R^3$ and $R^4$ are each independently selected from $C_{1-6}$ alkyl, nitro, amino or $C_{1-6}$ dialkylamino.

10. The method of claim 9, wherein R is selected from

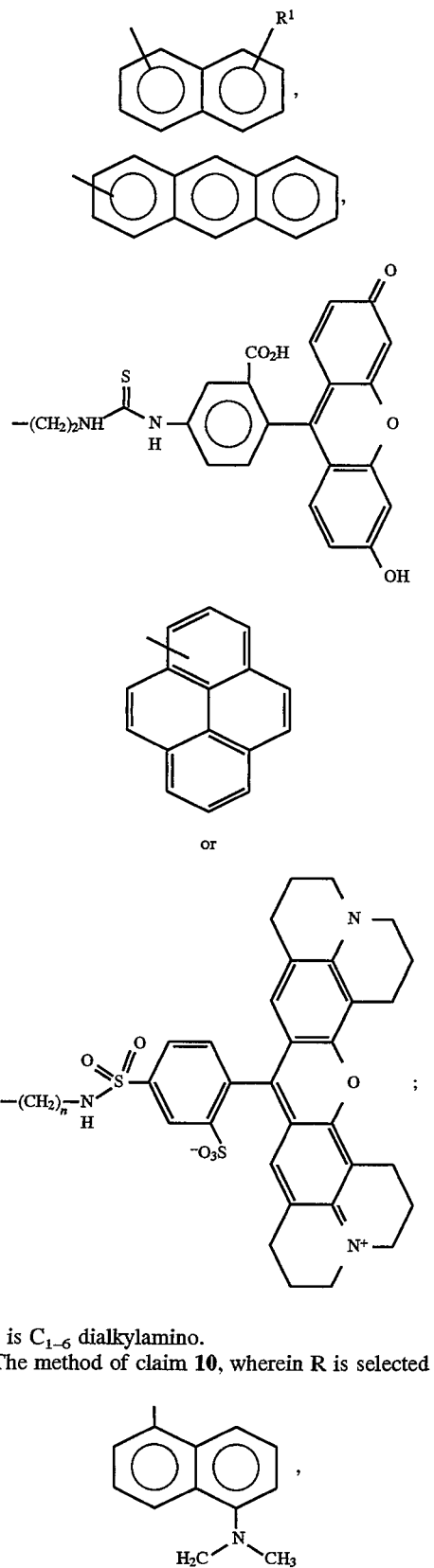

or and $R^1$ is $C_{1-6}$ dialkylamino.

11. The method of claim 10, wherein R is selected from

-continued

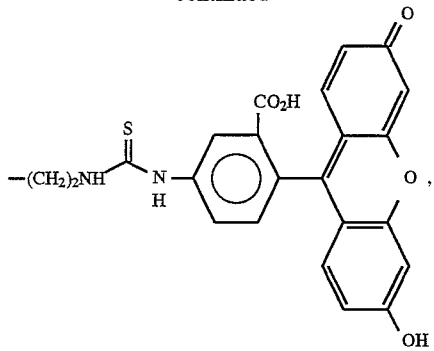

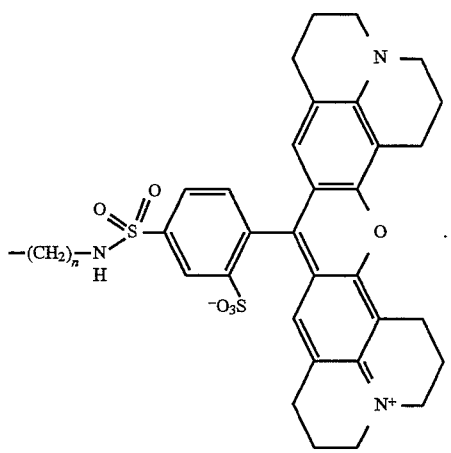

12. A method of monitoring GP IIb/IIIa receptor occupancy on platelets of a patient being treated with a GP IIb/IIIa inhibitor compound comprising taking a blood sample from the patient, measuring total fluorescence of a fluorescent probe compound of claim 1 which binds to the GP IIa/IIIb receptor, adding the fluorescent probe compound to the blood sample to bind the fluorescent probe compound to the GP IIb/IIIa receptor, measuring fluorescence of unbound fluorescent probe compound in the sample, measuring the difference between total fluorescence and unbound fluorescence, and identifying, based on a showing of difference between total fluorescence and unbound fluorescence, the level of receptor occupancy on platelets.

13. The method of claim 12, wherein R is selected from $C_{0-6}$ alkyl substituted with $R^5$, or a mono- or polycylic aromatic ring system that is either unsubstituted or substituted with one or more of $R^1$ and $R^2$.

14. The method of claim 13, wherein R is selected from

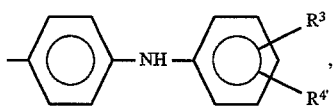

-continued

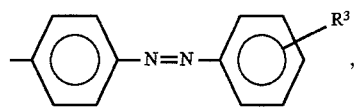

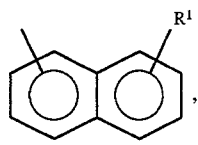

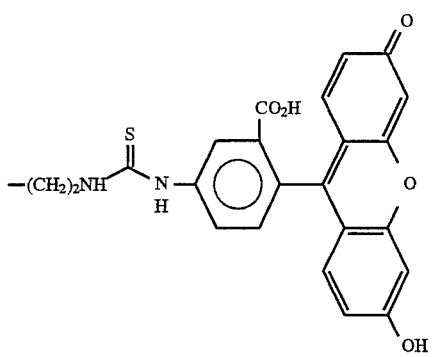

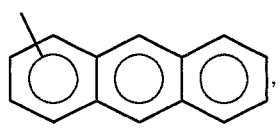

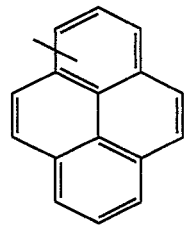

or

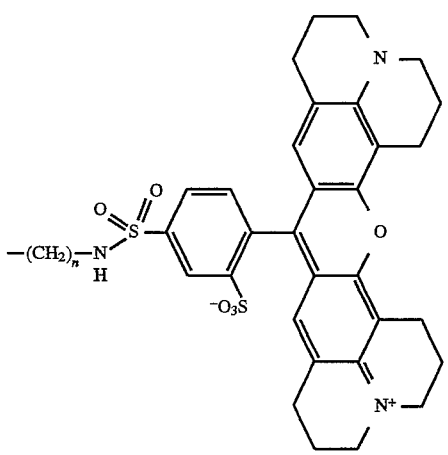

where n is an integer of from 0 to 6.

15. The method of claim 14, wherein $R^1$ is selected from $C_{1-6}$ dialkylamino, arylamino or aryl $C_{1-6}$ alkylamino; and $R^3$ and $R^4$ are each independently selected from $C_{1-6}$ alkyl, nitro, amino or $C_{1-6}$ dialkylamino.

16. The method of claim 15, wherein R is selected from

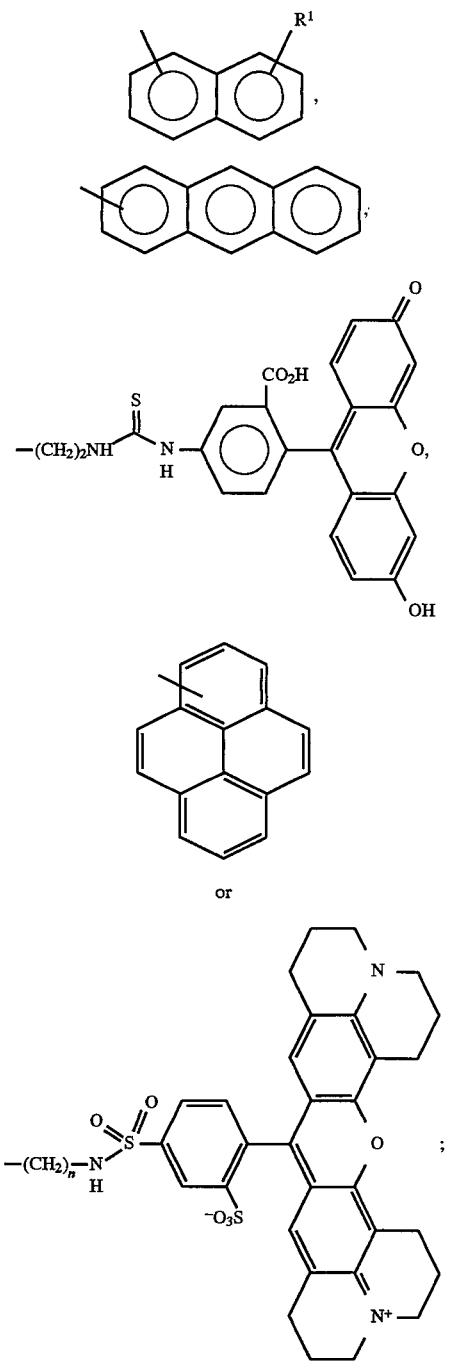

and $R^1$ is $C_{1-6}$ dialkylamino.

17. The method of claim 16, wherein R is selected from

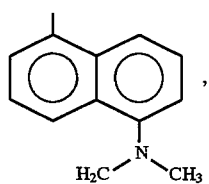

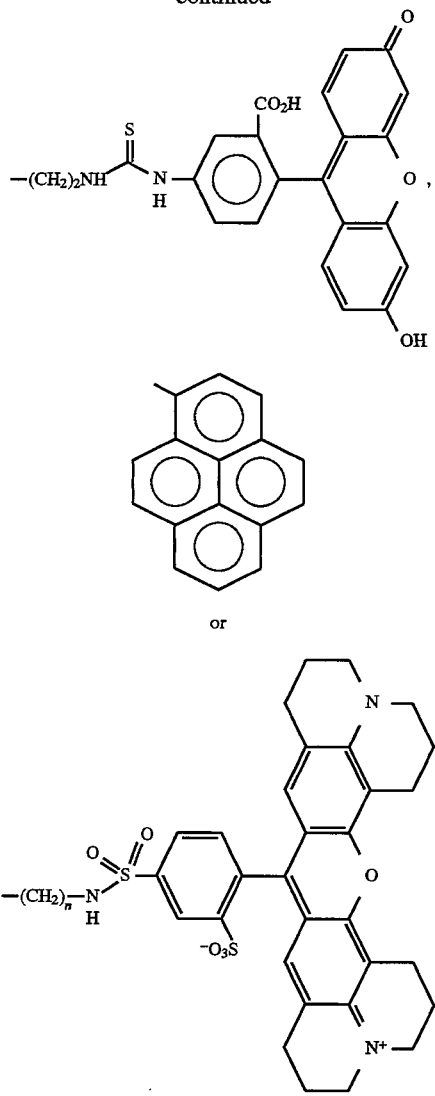

18. A method for identifying an antiplatelet agent that binds to unactivated platelets comprising mixing a fluorescent probe compound of claim 1 with an unactive form of GP IIb/IIIa receptor to bind the fluorescent probe compound to the unactive form of GP IIb/IIIa receptor, measuring fluorescence of fluorescent probe compound bound to GP IIb/IIIa receptor, displacing the bound fluorescent probe compound with a nonfluorescent antiplatelet agent by titrating with the nonfluorescent antiplatelet agent to form a titration solution comprising displaced probe compound and antiplatelet agent bound to the receptor, measuring fluorescence of the titration solution, determining difference in fluorescence between the fluorescence of fluorescent probe compound bound to unactive GP IIb/IIIa receptor and fluorescence of the titration solution, and identifying, based on a showing of difference between fluorescence of fluorescent probe compound bound to unactive GP IIb/IIIa receptor and fluorescence of the titration solution, an antiplatelet agent that binds to unactivated platelets.

19. The method of claim 18, wherein R is selected from $C_{0-6}$ alkyl substituted with $R^5$, or a mono- or polycylic aromatic ring system that is either unsubstituted or substituted with one or more of $R^1$ and $R^2$.

20. The method of claim 19, wherein R is selected from

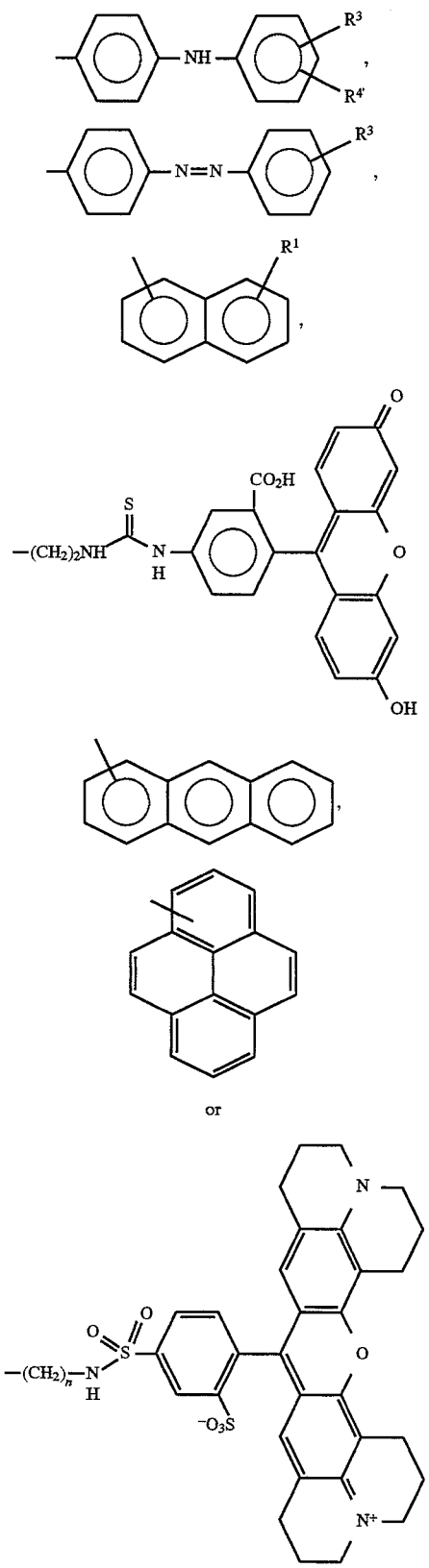

where n is an integer of from 0 to 6.

21. The method of claim 20, wherein $R^1$ is selected from $C_{1-6}$ dialkylamino, arylamino or aryl $C_{1-6}$ alkylamino; and $R^3$ and $R^4$ are each independently selected from $C_{1-6}$ alkyl, nitro, amino or $C_{1-6}$ dialkylamino.

22. The method of claim 21, wherein R is selected from

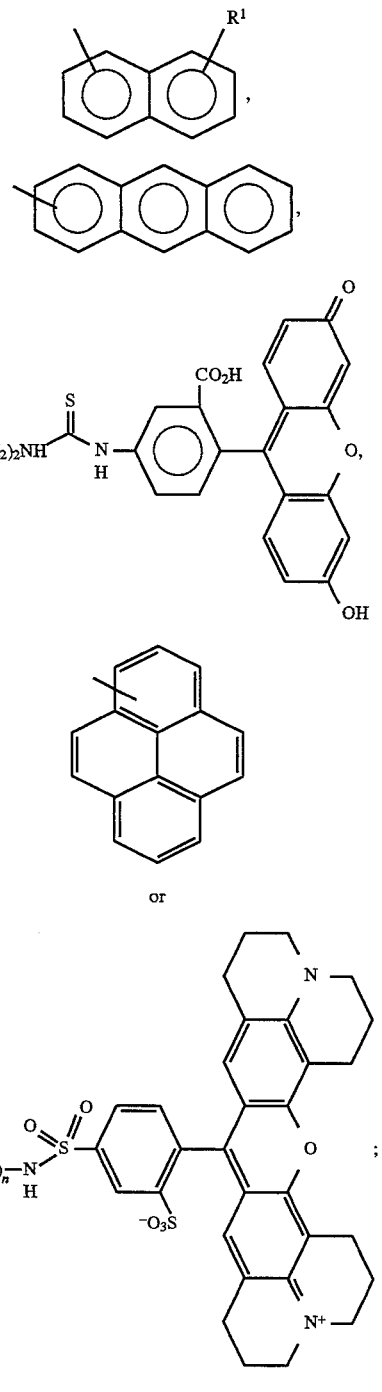

and $R^1$ is $C_{1-6}$ dialkylamino.

23. The method of claim 22, wherein R is selected from

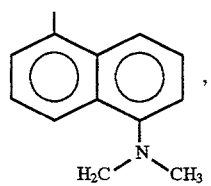

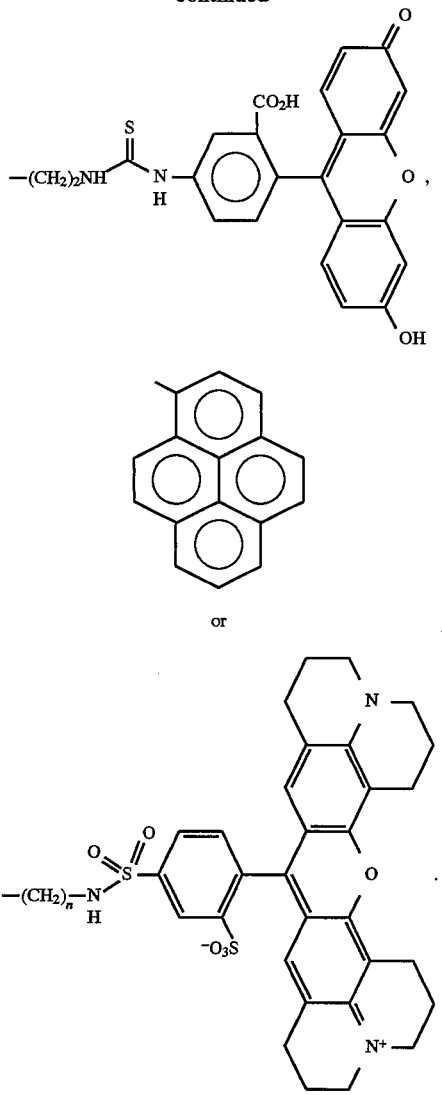

24. A method for determining preferential binding of an antiplatelet agent to activated or unactivated platelets comprising 1) mixing a fluorescent probe compound of claim 1 with an active form of GP IIb/IIIa receptor to bind the fluorescent probe compound to the active form of GP IIb/IIIa receptor, measuring fluorescence of fluorescent probe compound bound to active GP IIb/IIIa receptor, displacing the bound fluorescent probe compound with a nonfluorescent antiplatelet agent by titrating with the nonfluorescent antiplatelet agent to form a first titration solution comprising displaced probe compound and antiplatelet agent bound to the active receptor, measuring fluorescence of the first titration solution, determining difference in fluorescence between the fluorescence of fluorescent probe compound bound to active GP IIb/IIIa receptor and fluorescence of the first titration solution, and identifying, based on a showing of difference between fluorescence of fluorescent probe compound bound to active GP IIb/IIIa, receptor and fluorescence of the first titration solution, an antiplatelet agent that binds to activated platelets;

2) mixing the fluorescent probe compound with an unactive form of GP IIb/IIIa receptor to bind the fluorescent probe compound to the unactive form of GP IIb/IIIa receptor, measuring fluorescence of fluorescent probe compound bound to unactive GP IIb/IIIa receptor, displacing the bound fluorescent probe compound with the nonfluorescent antiplatelet agent by titrating with the nonfluorescent antiplatelet agent to form a second titration solution comprising displaced probe compound and antiplatelet agent bound to the unactive receptor, measuring fluorescence of the second titration solution, determining difference in fluorescence between the fluorescence of fluorescent probe compound bound to unactive GP IIb/IIIa receptor and fluorescence of the second titration solution, and identifying, based on a showing of difference between fluorescence of fluorescent probe compound bound to inactive GP IIb/IIIa receptor and fluorescence of the second titration solution, an antiplatelet agent that binds to unactivated platelets; and 3) identifying the greater of the difference obtained in 1) or the difference obtained in 2 to identify the receptor to which the antiplatelet agent preferentially binds.

* * * * *

UNITED STATES PATENT AND TRADEMARK OFFICE
CERTIFICATE OF CORRECTION

PATENT NO. : 5,646,000

DATED : 7/8/97

INVENTOR(S) : Bohumil Bednar, Melissa Egberton, Robert J. Gould, George D. Hartman and Jules A. Shafer It is certified that error appears in the above-indentified patent and that said Letters Patent is hereby corrected as shown below:

Column 46, line 51, please delete "antiolatelet" and insert -- antiplatelet --.

Signed and Sealed this

Twenty-fifth Day of November, 1997

Attest:

BRUCE LEHMAN

Attesting Officer

Commissioner of Patents and Trademarks